(12) United States Patent
Thompson et al.

(10) Patent No.: US 9,593,118 B2
(45) Date of Patent: Mar. 14, 2017

(54) XANTHINE-SUBSTITUTED ALKYNYL CARBAMATES/REVERSE CARBAMATES AS $A_2B$ ANTAGONISTS

(71) Applicant: Lewis and Clark Pharmaceuticals, Inc., Charlottesville, VA (US)

(72) Inventors: Robert D. Thompson, Charlottesville, VA (US); Anthony Beauglehole, Charlottesville, VA (US); Guoquan Wang, Crozet, VA (US)

(73) Assignee: Lewis and Clark Pharmaceuticals, Inc., Charlottesville, VA (US)

( * ) Notice: Subject to any disclaimer, the term of this patent is extended or adjusted under 35 U.S.C. 154(b) by 0 days.

(21) Appl. No.: 15/094,903

(22) Filed: Apr. 8, 2016

(65) Prior Publication Data

US 2016/0297819 A1    Oct. 13, 2016

Related U.S. Application Data

(60) Provisional application No. 62/144,371, filed on Apr. 8, 2015.

(51) Int. Cl.
*C07D 473/06*     (2006.01)
*A61K 31/522*     (2006.01)

(52) U.S. Cl.
CPC ................ *C07D 473/06* (2013.01)

(58) Field of Classification Search
None
See application file for complete search history.

(56) References Cited

U.S. PATENT DOCUMENTS

| 5,734,051 A | 3/1998 | Spicer et al. |
| 6,187,780 B1 | 2/2001 | Blech et al. |
| 7,253,176 B1 | 8/2007 | Waer et al. |
| 7,601,723 B2 | 10/2009 | Wang et al. |
| 2007/0072843 A1 | 3/2007 | Wang et al. |

FOREIGN PATENT DOCUMENTS

AU    B-37474/85    6/1985

OTHER PUBLICATIONS

Bedford, Simon T., et al., Discovery and optimization of potent and selective functional antagonists of human adenosine A2B receptor, Biorg. & Med. Chem. Lett. 2009, 19, 5945-9.

Cekic, Caglar, et al., Adenosine A2B Receptor Blockade Slows Growth of Bladder and Breast Tumors, J. Immunology 2012, 188, 1-8.

*Primary Examiner* — Brian J Davis
(74) *Attorney, Agent, or Firm* — Vance Intellectual Property, PC

(57) ABSTRACT

The present invention provides xanthine-substituted alkynyl carbamates/reverse carbamates and derivatives thereof and pharmaceutical compositions containing the same that are selective antagonists of $A_{2B}$ adenosine receptors (ARs). These compounds and compositions are useful as pharmaceutical agents.

21 Claims, No Drawings

XANTHINE-SUBSTITUTED ALKYNYL CARBAMATES/REVERSE CARBAMATES AS A₂B ANTAGONISTS

FIELD OF THE INVENTION

The present invention relates to xanthine-substituted alkynyl carbamates/reverse carbamates and pharmaceutical compositions thereof that are antagonists of $A_{2B}$ adenosine receptors (ARs). These compounds and compositions are useful as pharmaceutical agents.

BACKGROUND OF THE INVENTION

Antagonists of $A_{2B}$ adenosine receptors are indicated for a number of different uses, including asthma and chronic obstructive pulmonary disorder (COPD). Efforts have yielded selective and potent $A_{2B}$ antagonists. However, $A_{2B}$ antagonists (e.g., the xanthine-based CVT-6883) typically are not very soluble and concomitantly suffer from low bioavailability and poor tissue penetration (see, for example, Bedford, S. T. et al., Bioorg. Med. Chem. Lett. 2009, 19, 5945-9 and Wang, G. et al., U.S. Pat. No. 7,601,732).

Therefore, it is important to continue to synthesize and test additional $A_{2B}$ receptor antagonists in order to develop new and improved therapeutic agents.

SUMMARY OF THE INVENTION

Accordingly, in an aspect, the present invention provides novel xanthine-substituted alkynyl carbamates/reverse carbamates or pharmaceutically acceptable salts thereof that are $A_{2B}$ antagonists.

In another aspect, the present invention provides novel pharmaceutical compositions, comprising: a pharmaceutically acceptable carrier and a therapeutically effective amount of at least one of the compounds of the present invention or a stereoisomer or pharmaceutically acceptable salt form thereof.

In another aspect, the present invention provides methods of treating a pathological condition or symptom in a mammal for which the $A_{2B}$ receptor is implicated and antagonism of the receptor provides therapeutic benefit by administering to a subject an effective amount of a compound of the present invention.

In another aspect, the present invention provides methods of treating an adenosine $A_{2B}$ receptor-associated state in a subject by administering to the subject an effective amount of a compound of the present invention.

In another aspect, the present invention provides compounds for use in medical therapy.

In another aspect, the present invention provides the use of compounds of the present invention for the manufacture of a medicament for the treatment of a pathological condition or symptom in a mammal for which the $A_{2B}$ receptor is implicated and antagonism of the receptor provides therapeutic benefit.

These and other objects, which will become apparent during the following detailed description, have been achieved by the inventors' discovery that the presently claimed compounds or stereoisomers or pharmaceutically acceptable salt forms thereof are expected to be effective $A_{2B}$ antagonists.

DETAILED DESCRIPTION OF THE INVENTION

All references cited herein are hereby incorporated in their entirety herein by reference.

In an aspect, the present invention provides novel compounds of Formula I or II a stereoisomer or pharmaceutically acceptable salt thereof:

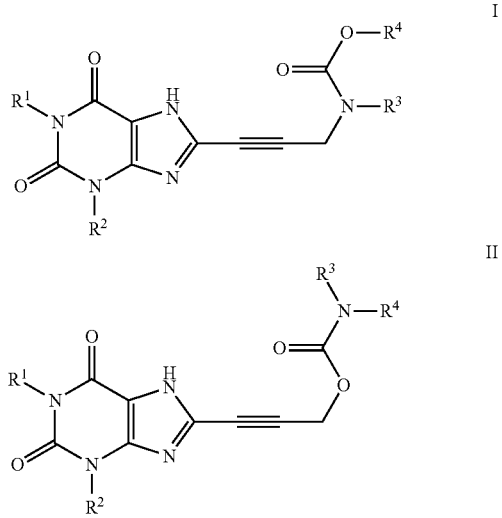

wherein:
$R^1$ is selected from: $C_{1-5}$ alkyl, $—C_{2-5}$ alkylene-OH, $—C_{2-5}$ alkylene-O—$C_{1-5}$ alkyl, $C_{3-6}$ cycloalkyl, $—C_{1-3}$ alkylene-$C_{3-6}$ cycloalkyl, $—CH_2—C_{2-4}$ alkenyl, $—CH_2—C_{2-4}$ alkynyl, and $—C_{3-6}$ cycloalkylene-O—$C_{1-3}$ alkyl;
$R^2$ is selected from: $C_{1-5}$ alkyl, $—C_{2-5}$ alkylene-OH, $—C_{2-5}$ alkylene-O—$C_{1-5}$ alkyl, $C_{3-6}$ cycloalkyl, $—C_{1-3}$ alkylene-$C_{3-6}$ cycloalkyl, $—CH_2—C_{2-4}$ alkenyl, $—CH_2—C_{2-4}$ alkynyl, and $—C_{3-6}$ cycloalkylene-O—$C_{1-3}$ alkyl;
$R^3$ is selected from: $C_{1-6}$ alkyl, $—C_{2-5}$ alkylene-O—$C_{1-5}$ alkyl, $—C_{2-5}$ alkylene-S—$C_{1-5}$ alkyl, $—C_{2-5}$ alkylene-$NR^aR^b$, $—C_{2-5}$ alkylene-OH, $—C_{2-5}$ alkylene-SH, $—C_{2-5}$ alkylene-$NR^aR^b$, $C_{3-6}$ cycloalkyl, and $—C_{1-3}$ alkylene-$C_{3-6}$ cycloalkyl;
$R^4$ is selected from: phenyl and 5-6 membered heteroaryl;
the phenyl and heteroaryl groups of $R^4$ are optionally substituted with 1-3 groups independently selected from: $C_{1-4}$ alkyl, $C_{3-6}$ cycloalkyl, $—C_{1-3}$ alkylene-$C_{3-6}$ cycloalkyl, F, Cl, Br, I, $—CN$, $OR^a$, $SR^a$, $NR^aR^b$, $CF_3$, $OCF_3$, $COR^a$, $CO_2R^a$, $C(O)NR^aR^b$, $OC(O)R^a$, $OCO_2R^a$, $OC(O)NR^aR^b$, $NR^bCOR^a$, $NR^bCO_2R^a$, $NR^bC(O)NR^aR^b$, and $S(O)_pNR^aR^b$;
each $R^a$ is independently selected from: H, $C_{1-8}$ alkyl, $C_{3-6}$ cycloalkyl, and $—C_{1-3}$ alkylene-$C_{3-6}$ cycloalkyl;
each $R^b$ is independently selected from: H, $C_{1-8}$ alkyl, $C_{3-6}$ cycloalkyl, and $—C_{1-3}$ alkylene-$C_{3-6}$ cycloalkyl;
alternatively, each $NR^aR^b$ group is optionally selected from a 3-6 membered cyclic amine; and,
p is independently selected from: 0, 1, and 2.

In another aspect, the compound is of Formula I or a stereoisomer or pharmaceutically acceptable salt thereof.

In another aspect, the compound is of Formula I or a stereoisomer or pharmaceutically acceptable salt thereof, wherein:

$R^1$ is selected from: $C_{1-3}$ alkyl and $C_{3-6}$ cycloalkyl;

$R^2$ is selected from: $C_{1-3}$ alkyl and $C_{3-6}$ cycloalkyl;

$R^3$ is selected from: $C_{1-6}$ alkyl and —$C_{1-3}$ alkylene-$C_{3-6}$ cycloalkyl;

$R^4$ is selected from: phenyl and 5-6 membered heteroaryl;

the phenyl and heteroaryl groups of $R^4$ are optionally substituted with 1-2 groups independently selected from: $C_{1-4}$ alkyl, $C_{3-6}$ cycloalkyl, —$C_{1-3}$ alkylene-$C_{3-6}$ cycloalkyl, F, Cl, Br, I, —CN, $OR^a$, $SR^a$, $NR^aR^b$, $CF_3$, $OCF_3$, $COR^a$, $CO_2R^a$, $C(O)NR^aR^b$, $OC(O)R^a$, $OCO_2R^a$, $OC(O)NR^aR^b$, $NR^bCOR^a$, $NR^bCO_2R^a$, $NR^bC(O)NR^aR^b$, and $S(O)_pNR^aR^b$;

each $R^a$ is independently selected from: H, $C_{1-4}$ alkyl, $C_{3-6}$ cycloalkyl, and —$C_{1-3}$ alkylene-$C_{3-6}$ cycloalkyl;

each $R^b$ is independently selected from: H, $C_{1-4}$ alkyl, $C_{3-6}$ cycloalkyl, and —$C_{1-3}$ alkylene-$C_{3-6}$ cycloalkyl; and, p is independently selected from: 0, 1, and 2.

In another aspect, the compound is of Formula I or a stereoisomer or pharmaceutically acceptable salt thereof, wherein:

ring $R^4$ is selected from phenyl, pyridyl, thienyl, furanyl, pyrrolyl, oxazolyl, isoxazolyl, thiazolyl, isothiazolyl, pyrimidyl, and pyridazinyl.

In another aspect, the compound is of Formula I or a stereoisomer or pharmaceutically acceptable salt thereof, wherein:

ring $R^4$ is selected from phenyl and pyridyl.

In another aspect, the compound is of Formula I or a stereoisomer or pharmaceutically acceptable salt thereof, wherein:

$R^1$ is selected from: methyl, ethyl, and cyclopropyl;

$R^2$ is selected from: methyl, ethyl, and cyclopropyl;

$R^3$ is selected from: methyl, ethyl, and -methylene-cyclopropyl;

$R^4$ is phenyl optionally substituted with 1-2 groups independently selected from: $C_{1-4}$ alkyl, $C_{3-6}$ cycloalkyl, —$C_{1-3}$ alkylene-$C_{3-6}$ cycloalkyl, F, Cl, —CN, $OR^a$, $NR^aR^b$, $CF_3$, and $OCF_3$;

each $R^a$ is independently selected from: H, methyl, and ethyl; and, each $R^b$ is independently selected from: H, methyl, and ethyl.

In another aspect, the compound is selected from compounds 1-6:

1

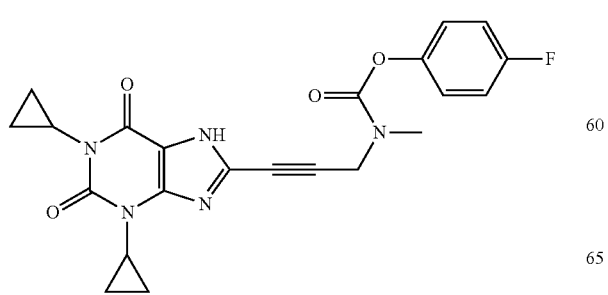

2

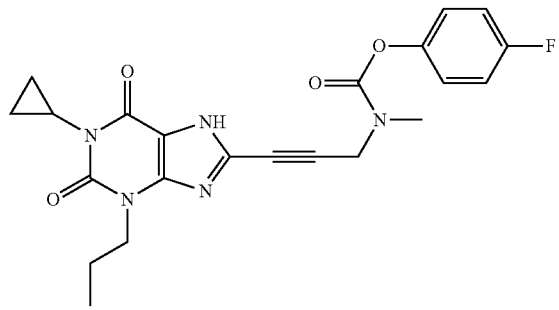

3

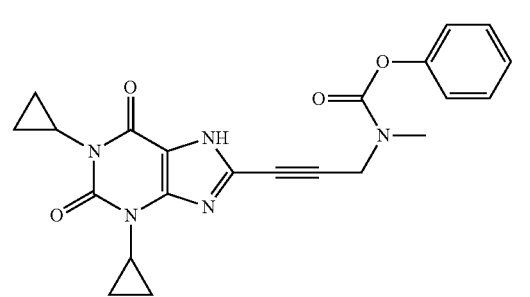

4

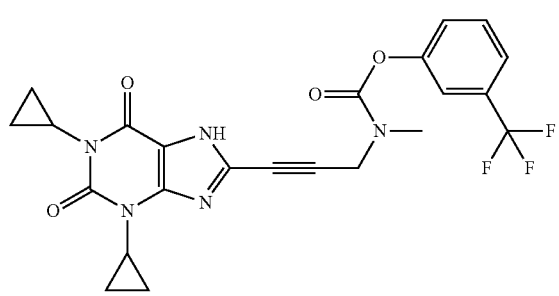

5

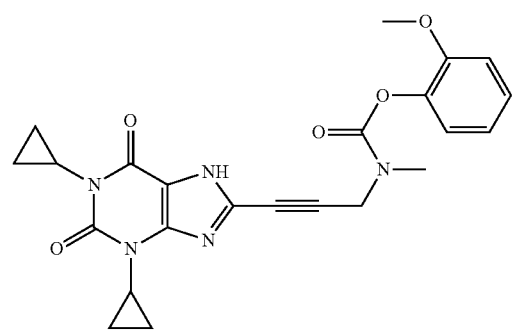

6

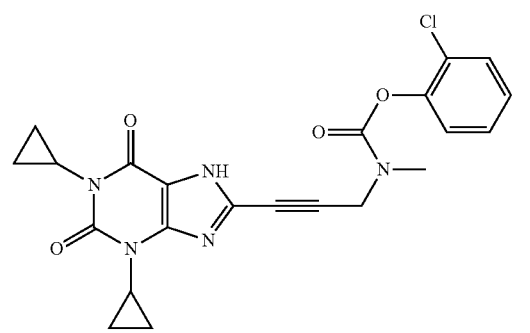

or a pharmaceutically acceptable salt thereof.

In another aspect, the compound is of Formula II or a stereoisomer or pharmaceutically acceptable salt thereof.

In another aspect, the compound is of Formula II or a stereoisomer or pharmaceutically acceptable salt thereof, wherein:

$R^1$ is selected from: $C_{1-3}$ alkyl and $C_{3-6}$ cycloalkyl;
$R^2$ is selected from: $C_{1-3}$ alkyl and $C_{3-6}$ cycloalkyl;
$R^3$ is selected from: $C_{1-6}$ alkyl and —$C_{1-3}$ alkylene-$C_{3-6}$ cycloalkyl;
$R^4$ is selected from: phenyl and 5-6 membered heteroaryl;
the phenyl and heteroaryl groups of $R^4$ are optionally substituted with 1-2 groups independently selected from: $C_{1-4}$ alkyl, $C_{3-6}$ cycloalkyl, —$C_{1-3}$ alkylene-$C_{3-6}$ cycloalkyl, F, Cl, Br, I, —CN, $OR^a$, $SR^a$, $NR^aR^b$, $CF_3$, $OCF_3$, $COR^a$, $CO_2R^a$, $C(O)NR^aR^b$, $OC(O)R^a$, $OCO_2R^a$, $OC(O)NR^aR^b$, $NR^bCOR^a$, $NR^bCO_2R^a$, $NR^bC(O)NR^aR^b$, and $S(O)_pNR^aR^b$;
each $R^a$ is independently selected from: H, $C_{1-4}$ alkyl, $C_{3-6}$ cycloalkyl, and —$C_{1-3}$ alkylene-$C_{3-6}$ cycloalkyl;
each $R^b$ is independently selected from: H, $C_{1-4}$ alkyl, $C_{3-6}$ cycloalkyl, and —$C_{1-3}$ alkylene-$C_{3-6}$ cycloalkyl; and,
p is independently selected from: 0, 1, and 2.

In another aspect, the compound is of Formula II or a stereoisomer or pharmaceutically acceptable salt thereof, wherein:

ring $R^4$ is selected from phenyl, pyridyl, thienyl, furanyl, pyrrolyl, oxazolyl, isoxazolyl, thiazolyl, isothiazolyl, pyrimidyl, and pyridazinyl.

In another aspect, the compound is of Formula II or a stereoisomer or pharmaceutically acceptable salt thereof, wherein:

ring $R^4$ is selected from phenyl and pyridyl.

In another aspect, the compound is of Formula II or a stereoisomer or pharmaceutically acceptable salt thereof, wherein:

$R^1$ is selected from: methyl, ethyl, and cyclopropyl;
$R^2$ is selected from: methyl, ethyl, and cyclopropyl;
$R^3$ is selected from: methyl, ethyl, and -methylene-cyclopropyl;
$R^4$ is phenyl optionally substituted with 1-2 groups independently selected from: $C_{1-4}$ alkyl, $C_{3-6}$ cycloalkyl, —$C_{1-3}$ alkylene-$C_{3-6}$ cycloalkyl, F, Cl, —CN, $OR^a$, $NR^aR^b$, $CF_3$, and $OCF_3$;
each $R^a$ is independently selected from: H, methyl, and ethyl; and,
each $R^b$ is independently selected from: H, methyl, and ethyl.

In another aspect, the compound is selected from compounds 7-8:

7

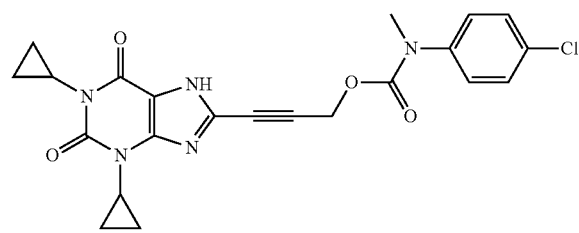

8

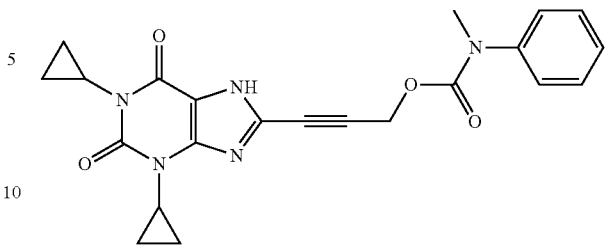

or a pharmaceutically acceptable salt thereof.

In another aspect, the present invention provides a novel compound of Formula I or II, or a stereoisomer or pharmaceutically acceptable salt thereof, wherein: one or more H are replaced by D. For example, $R^1$ can be a deuterated methyl group (e.g., $CD_3$) or the alkynyl hydrogens can be replaced by deuterium (—$CD_2$-). In addition, the groups recited in $R^1$, $R^2$, $R^3$, $R^4$, $R^a$, and $R^b$ that contain a hydrogen (e.g., alkyl, cycloalkyl, alkylene, aryl, and heteroaryl) can be partially or fully replaced by D (e.g., $CD_3$, $CD_2CD_3$, $CD_2CD(CD_3)_2$, $d_5$-cyclopropyl, $d_7$-cyclobutyl, $d_9$-cyclopentyl, $d_5$-cyclopropyl-$CD_2$, $d_5$-phenyl, $d_4$-phenyl (one substituent is present), $d_3$-phenyl (two substituents are present), $d_4$-pyridyl, $d_3$-pyridyl (one substituent is present), and $d_2$-pyridyl (two substituent are present).

In another aspect, the present invention provides a novel compound of Formula I or II, wherein the compound is a deuterium-enriched compound of $I_1$-$II_1$ or a stereoisomer or pharmaceutically acceptable salt thereof:

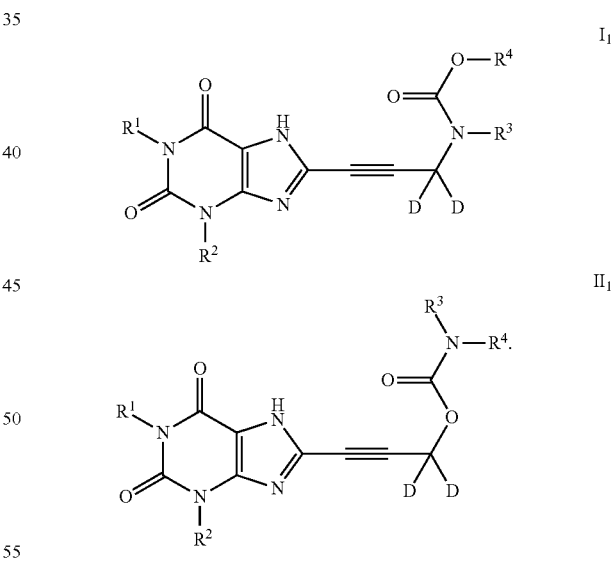

Deuterium-enriched compounds of the present invention can be prepared by a number of known methods including deuterium exchange of acid labile hydrogens (e.g., contacting the compound with NaOD in $D_2O$) and using deuterated starting materials (e.g., deuterated iodo-adenosine-uronamide).

In another aspect, the present invention provides a novel pharmaceutical composition, comprising: a therapeutically effective amount of a compound of the present invention or a stereoisomer or pharmaceutically acceptable salt thereof and a pharmaceutically acceptable carrier.

In another aspect, the present invention provides a method for treating an adenosine $A_{2B}$ receptor associated state in a subject, comprising: administering to the subject therapeutically effective amount of a compound of the present invention or a stereoisomer or pharmaceutically acceptable salt thereof.

In another aspect, the adenosine $A_{2B}$ receptor associated state is selected from asthma, bronchoconstriction, chronic obstructive pulmonary disorder (COPD), angiogenesis, pulmonary fibrosis, emphysema, allergies, allergic diseases (e.g. allergic rhinitis (e.g., (perennial, seasonal, and occupational) and sinusitis), autoimmune diseases, inflammation, atherosclerosis, hypertension, congestive heart failure, retinopathy, diarrheal diseases, insulin resistance, Type 1 diabetes, Type 2 diabetes, obesity, fatty liver disease, pain (e.g., nociceptive pain), wound healing, inflammatory gastrointestinal tract disorders (e.g., inflammatory bowel disease), sickle cell disease, cancer (e.g., bladder (e.g., MB49 cell line) and breast (e.g., 4T1-12B cell line)), heart attack, diabetic retinopathy, hyperbaric oxygen-induced retinopathy, inhibition of angiogenesis in neoplastic tissues, gastrointestinal disorders, immunological disorders, hypersensitivity disorders, neurological disorders, and cardiovascular diseases due to both cellular hyperproliferation and apoptosis.

In another aspect, the state is an autoimmune disease selected from: Addison's disease, autoimmune hemolytic anemia, Crohn's disease, Goodpasture's syndrome, Graves' disease, Hashimoto's thyroiditis, idiopathic thrombocytopenic purpura, multiple sclerosis, myasthenia gravis, pemphigus vulgaris, pernicious anemia, poststreptococcal glomerulonephritis, psoriasis, rheumatoid arthritis, scleroderma, Sjogren's syndrome, spontaneous infertility, and systemic lupus erythematosus.

In another aspect, the adenosine $A_{2B}$ receptor associated state is selected from: asthma, insulin resistance, atherosclerosis, fatty liver disease, bladder cancer, and breast cancer.

In another aspect, the adenosine $A_{2B}$ receptor associated state is asthma.

In another aspect, the adenosine $A_{2B}$ receptor associated state is insulin resistance.

In another aspect, the adenosine $A_{2B}$ receptor associated state is atherosclerosis.

In another aspect, the adenosine $A_{2B}$ receptor associated state is fatty liver disease.

In another aspect, the adenosine $A_{2B}$ receptor associated state is bladder cancer.

In another aspect, the adenosine $A_{2B}$ receptor associated state is breast cancer.

In another aspect, the adenosine $A_{2B}$ receptor associated state is human cell line MDA-MB-231 breast cancer.

In another aspect, the present invention provides a compound for use in therapy.

In another aspect, the present invention provides the use of compounds for the manufacture of a medicament for the treatment of an indication recited herein.

In another aspect, examples of the molecular weight of the compounds of the present invention include (a) less than about 500, 550, 600, 650, 700, 750, 800, 850, 900, 950, or 1000 grams per mole; (b) less than about 950 grams per mole; (c) less than about 850 grams per mole; and, (d) less than about 750 grams per mole.

In another aspect, examples of the solubility of the compounds of the present invention include greater than 50 60, 70, 80, 90, 100, 110, 120, 130, 140, 150, 160, 170, 180, 190, 200, 210, 220, 230, 240, 250, 260, 270, 280, 290, 300, 400, 500, 600, 700, 800, 900 and 1000 µg/mL.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

A compound or compounds of the present invention, as used herein, includes, where appropriate, stereoisomers and/or pharmaceutically acceptable salts thereof.

"Adenosine $A_{2B}$ receptor antagonist" includes compounds that deactivate the adenosine $A_{2B}$ receptor with a $K_i$ of <1 µM as determined by a known binding assay. An adenosine $A_{2B}$ receptor agonist may also be cross reactive with other adenosine receptor subtypes (e.g., $A_1$, $A_{2A}$, and $A_3$). In one embodiment, the adenosine $A_{2B}$ receptor agonist may be selective for $A_{2B}$ (e.g., at least 2, 10, 50, or 100/1 over another adenosine receptor subtype) or may activate/antagonize other receptors with a greater or lesser affinity than the $A_{2B}$ receptor.

"Adenosine $A_{2B}$ receptor associated state" includes those diseases or disorders which are directly or indirectly implicated in the adenosine $A_{2B}$ receptor pathway. Without being bound by theory, it is thought that administration of an adenosine $A_{2B}$ antagonist blocks the biological activity of natural adenosine at the $A_{2B}$ receptor. Accordingly, an adenosine $A_{2B}$ receptor associated state includes those diseases and disorders directly associated with the activity of the adenosine $A_{2B}$ receptor or the activity of the biological pathway associated with the adenosine $A_{2B}$ receptor.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

"Stable" means that the compound is suitable for pharmaceutical use.

The present invention covers stable compounds and thus avoids, unless otherwise specified, the following bond types: heteroatom-halogen, N—S, O—S, O—O, and S—S.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

When an "ene" terminates a group it indicates the group is attached to two other groups. For example, methylene refers to a —$CH_2$-moiety.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$alkenyl includes $C_2$, $C_3$, $C_4$, $C_5$, and $C_6$alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$Alkynyl includes $C_2$, $C_3$, $C_4$, $C_5$, and $C_6$alkynyl groups.

"Alkoxy" includes alkyl, alkenyl, and alkynyl groups covalently linked to an oxygen atom. Examples of alkoxy groups include methoxy, ethoxy, isopropyloxy, propoxy, t-butyloxy, isobutyloxy, butoxy, and pentoxy groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

"Halo" or "halogen" refers to fluoro, chloro, bromo, and iodo.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, adamantyl, and tetrahydronaphthyl.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), $S(O)_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Mammal" and "patient" cover warm blooded mammals that are typically under medical care (e.g., humans and domesticated animals). Examples include feline, canine, equine, bovine, non-human primate, and human, as well as just human.

"Treating" or "treatment" covers the treatment of a disease-state in a mammal, and includes: (a) inhibiting the disease-state, e.g., arresting its development; and/or (b) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to an indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Formulations and Dosages

The compounds of the present invention can be formulated as pharmaceutical compositions and administered to a mammalian host, such as a human patient in a variety of forms adapted to the chosen route of administration, e.g., orally or parenterally, by intravenous (e.g., continuously or bolus), intrathecal, intramuscular, topical, intradermal, intraperitoneal, intraocular, inhalation or subcutaneous routes. Exemplary pharmaceutical compositions are disclosed in "*Remington: The Science and Practice of Pharmacy*," A. Gennaro, ed., 20th edition, Lippincott, Williams & Wilkins, Philadelphia, Pa.

Thus, the present compounds may be systemically administered, e.g., orally, in combination with a pharmaceutically acceptable carrier/excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The amount of active compound in such therapeutically useful compositions is such that an effective dosage level will be obtained.

The amount of the compound of the present invention or an active salt or derivative thereof, required for use in treatment will vary not only with the particular compound or salt selected but also with the route of administration, the nature of the condition being treated, and the age and condition of the patient, and will ultimately be at the discretion of the attendant physician or clinician. In general, however, a suitable dose will be in the range of (a) about 1.0-1000 mg/kg of body weight per day, (b) about 10-500 mg/kg of body weight per day, and (c) about 5-20 mg/kg of body weight per day.

For an eye drop, the composition will typically contain an active ingredient at a concentration of generally from 0.000001 to 10% (w/v), also from 0.00001 to 3% (w/v), 0.0001 to 1% (w/v), and 0.001 to 0.1% (w/v) may be instilled to an adult once to several times a day.

For oral administration, the compounds of the present invention may be administered to an adult once or divided into several times at a dose of generally from 0.001 to 5000 mg per day, also from 0.1 to 2500 mg per day, and from 1 to 1000 mg per day.

For a liquid composition (e.g., in a lotion), the concentration of compounds of the present invention can be from (a) about 0.1-25 wt % and (b) about 0.5-10 wt %. The concentration in a semi-solid or solid composition such as a gel or a powder can be (a) about 0.1-5 wt % and (b) about 0.5-2.5 wt %.

The compounds of the present invention can be conveniently administered in unit dosage form; e.g., tablets, caplets, etc., containing (a) about 4-400 mg, (b) about 10-200 mg, and (c) about 20-100 mg of active ingredient per unit dosage form.

The compounds of the present invention can be administered to achieve peak plasma concentrations of the active compound of (a) about 0.02-20 µM, (b) about 0.1-10 µM, and (c) about 0.5-5 µM. These concentrations may be achieved, for example, by the intravenous injection (e.g., continuously or bolus) of a 0.005-0.5% solution of the active ingredient, or orally administered as a bolus containing about 4-400 mg of the active ingredient.

When a compound of the present invention is administered in combination with another agent or agents (e.g., co-administered), then the compound of the present invention and other agent can be administered simultaneously or in any order. They can be administered as a single pharmaceutical composition or as separate compositions. The administration of the compound of the present invention can be prior to the other agent(s), within minutes thereof, or up to hours (e.g., 24 or 48) or even days after the administration of the other agent(s). For example, the administration of the compound of the present invention can be within about 24 hours or within about 12 hours.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds of the present invention may also be administered intravenously (e.g., continuously or bolus) or intraperitoneally by infusion or injection. Solutions of the compounds of the present invention or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds of the present invention may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The compounds of the present invention can also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, and atomizers are fully described in pharmaceutical reference books such as *Remington's Pharmaceutical Sciences* Volumes 16 (1980) or 18 (1990) Mack Publishing Co.

The desired dose of the compounds of the present invention may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Useful methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

One stereoisomer of a compound of the present invention may be a more potent $A_{2B}$ antagonist than its counterpart(s). Thus, stereoisomers are included in the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the present invention may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Other features of the invention will become apparent in the course of the following descriptions of exemplary embodiments that are given for illustration of the invention and are not intended to be limiting thereof.

EXAMPLES

The following examples are representative of the procedures used to prepare the compounds of the present invention.

Procedure for the synthesis of 1,3-dicyclopropylxanthine

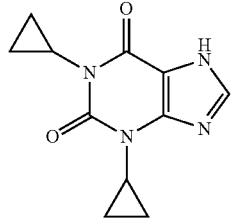 [SMILES: O=c1c2[nH]cnc2n(C2CC2)c(=O)n1C1CC1]

6-amino-1,3-dicyclopropyl-5-nitrosopyrimidine-2,4-dione (10.0 g, 42.33 mmoles) was suspended in methanol (150 mL). 10% Pd/C (1.30 g, wet weight) was added. The mixture was stirred under hydrogen at 20 psi overnight. After filtration, the mother liquid was concentrated and dried under vacuum to give the intermediate diamine compound. The diamine compound was suspended in triethyl orthoformate (83 mL) in a pressure tube, stirred at room temperature overnight and at 140° C. for 4 hours. After cooling, the solid was filtered and washed with ether to give 9.2 g, 41.3 mmoles, 97% yield.

Procedure for the synthesis of 1-cyclopropyl-3-propylxanthine

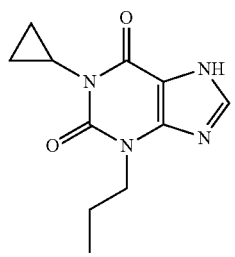 [SMILES: CCCn1c(=O)n(C2CC2)c(=O)c2[nH]cnc21]

6-amino-3-cyclopropyl-1-propyl-5-nitrosopyrimidine-2,4-dione (3.0 g, 12.59 mmoles) was suspended in methanol (50 ml). 10% Pd/C (0.50 g, wet weight) was added. The mixture was stirred under hydrogen at 20 psi overnight. After filtration, the mother liquid was concentrated and dried under vacuum to give the intermediate diamine compound. The diamine compound was suspended in triethyl orthoformate (30 ml) in a pressure tube, stirred at room temperature overnight, and at 140° C. for four hours. After cooling, the solid was filtered and washed with ether to give 2.6 g, 11.10 mmoles, 88% yield.

Procedure for the synthesis of 1,3-dicyclopropyl-8-iodoxanthine

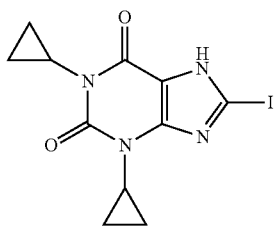 [SMILES: O=c1c2[nH]c(I)nc2n(C2CC2)c(=O)n1C1CC1]

1,3-Dicyclopropylxanthine (4 g, 17.2 mmoles) and N-iodosuccinimide (5.8 g, 25.8 mmoles) were added to DMF (dimethylformamide)(20 mL) and acetonitrile (60 mL). The mixture was stirred at room temperature (rt) for 72 hours. The acetonitrile solvent was removed in volume in vacuo. Next, the solids were filtered, washed with acetonitrile, and collected. The mother liquor was left at rt for 72 hours and the resulting precipitate collected. The solids were filtered and washed with acetonitrile. The combined product was boiled in acetonitrile and filtered to give 3.7 g, 10.30 mmoles, 60% yield.

Procedure for the synthesis of 1-cyclopropyl-3-propyl-8-iodoxanthine

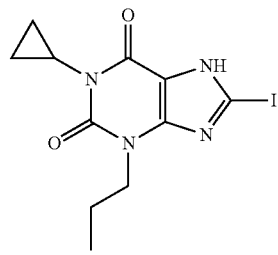 [SMILES: CCCn1c(=O)n(C2CC2)c(=O)c2[nH]c(I)nc21]

1-cyclopropyl-3-propylxanthine (1.81 g, 7.73 mmoles) and N-iodosuccinimide (2.59 g, 11.50 mmoles) were added to DMF (15 ml) and acetonitrile (30 mL). The mixture was stirred at room temperature (rt) for 72 hours. The acetonitrile solvent was removed in volume in vacuo. Next, the solids were filtered, washed with acetonitrile and collected. The mother liquor sat at rt for 72 hours precipitating more product. The solids were filtered and washed with acetonitrile. The combined product was boiled in acetonitrile and filtered to give 840 mg, 2.33 mmoles, 30% yield.

General Procedures for the Synthesis of Alkynes:

Method A) Aryl N-alkyl-N-(prop-2-yn-1-yl)carbamates

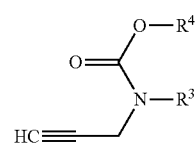

A mixture of N-alkylpropargylamine (1 equivalent) and pyridine (2.1 equivalents) in dry DCM (dichloromethane) (50 vol) was cooled over ice. Aryl chloroformate (1.1 equivalents) was added portion-wise slowly. The ice was removed, and the mixture stirred at 25° C. for 47 hrs. The mixture was poured into ice water (200 vol) and extracted with DCM (3×100 vol). The organic phases were combined and washed with brine (2×100 vol), dried over $MgSO_4$, filtered, and evaporated to dryness to afford the crude product, which was purified by silica column chromatography, eluting with EtOAc/hexanes gradient. Like fractions were collected, and the solvent removed in vacuo to give product. If necessary, a second column can be run eluting with EtOAc/hexanes gradient. Like fractions were collected, and the solvent removed in vacuo to give product.

Method B) Prop-2-yn-1-yl N-alkyl-N-arylcarbamate

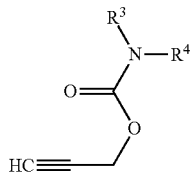

A mixture of N-alkylaminoaromatic compound (1 equivalent) and pyridine (2 equivalents) in DCM (42 vol) was cooled over ice. Propargyl chloroformate (1.2 equivalents) was added portion-wise slowly. The ice was removed and the mixture stirred at 25° C. for 21 hrs. The mixture was poured into ice water (150 vol) and extracted with DCM (3×80 vol). The organic phases were combined and washed with brine (2×80 vol), dried over MgSO$_4$, filtered, and evaporated to dryness to afford the crude product, which was purified by silica column chromatography, eluting with EtOAc/hexanes gradient. Like fractions were collected, and the solvent removed in vacuo to give product.

Example A1

Phenyl N-methyl-N-(prop-2-yn-1-yl)carbamate

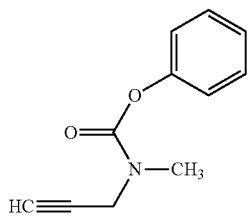

N-methylpropargylamine (0.45 mL, 5.33 mmoles), pyridine (0.9 mL, 11.17 mmoles) and phenyl chloroformate (0.75 mL, 5.98 mmoles). Column chromatography (Si=43 g), eluting with EtOAc (2-6%)/hexanes. A second column (Si=43 g) eluting with EtOAc (1-4%)/hexanes to give 0.626 g, 3.31 mmoles, 62% yield.

Example A2

4-Fluorophenyl N-methyl-N-(prop-2-yn-1-yl)carbamate

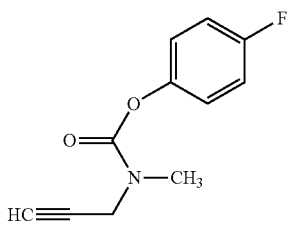

N-Methylpropargylamine (0.67 g, 10.99 mmoles), pyridine (1.60 mL, 19.86 mmoles) and 4-fluorophenyl chloroformate (2.38 g, 12.75 mmoles). Column chromatography (Si=43 g), eluting with 100% DCM to give 2.0 g, 9.12 mmoles, 83% yield.

Example A3

3-(Trifluoromethyl)phenyl N-methyl-N-(prop-2-yn-1-yl)carbamate

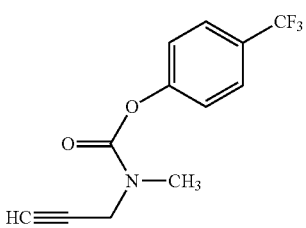 [SMILES: C#CCN(C)C(=O)Oc1ccc(C(F)(F)F)cc1]

N-methylpropargylamine (0.35 mL, 4.15 mmoles), pyridine (0.7 mL, 8.69 mmoles) and 3-(trifluoromethyl)phenyl chloroformate (0.73 mL, 4.70 mmoles). Column chromatography (Si=75 g), eluting with EtOAc (2-4%)/hexanes to give 0.69 g, 2.70 mmoles, 65% yield.

Example A4

2-Methoxyphenyl N-methyl-N-(prop-2-yn-1-yl)carbamate

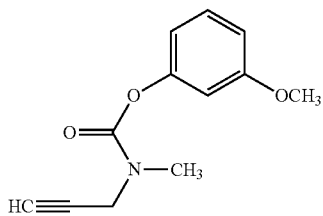

N-Methylpropargylamine (0.67 g, 10.99 mmoles), pyridine (1.60 mL, 19.86 mmoles) and 2-methoxyphenyl chloroformate (2.38 g, 12.75 mmoles). Column chromatography (Si=75 g), eluting with 100% DCM to give 2.0 g, 2.70 mmoles, 83% yield.

Example A5

2-Chlorophenyl N-methyl-N-(prop-2-yn-1-yl)carbamate

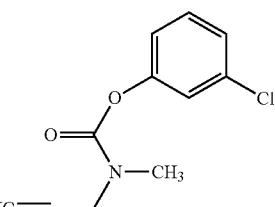

N-methylpropargylamine (0.4 mL, 4.74 mmoles), pyridine (0.8 mL, 9.93 mmoles) and 2-chlorophenyl chloroformate (0.75 mL, 5.38 mmoles). Column chromatography (Si=75 g), eluting with EtOAc (2-5%)/hexanes to give 0.6 g, 2.69 mmoles, 57% yield.

Example B1

Prop-2-yn-1-yl N-methyl-N-phenylcarbamate

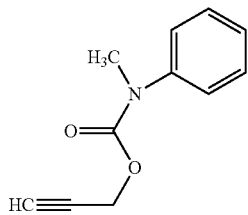

N-methylaniline (0.6 mL, 5.54 mmoles), pyridine (0.9 mL, 11.17 mmoles) and propargyl chloroformate (0.65 mL, 6.66 mmoles) in DCM (25 mL). Column chromatography (Si=75 g), eluting with EtOAc (0-7%)/hexanes to give 1.1 g, 5.82 mmoles, 105% yield.

Example B2

Prop-2-yn-1-yl N-4-chlorophenyl-N-methylcarbamate

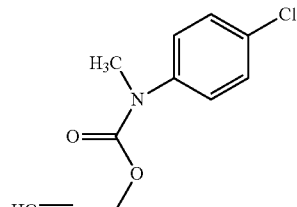

4-Chloro-N-methylaniline (0.74 mL, 5.73 mmoles), pyridine (1.10 mL, 13.60 mmoles) and propargyl chloroformate (0.650 mL, 6.66 mmoles) in DCM (25 mL). Column chromatography (Si=43 g), eluting with EtOAc (0-5%)/hexanes to give 700 mg, 3.13 mmol, 55% yield.

General procedure for the synthesis of 8-alkynyl-1,3-dialkylxanthine

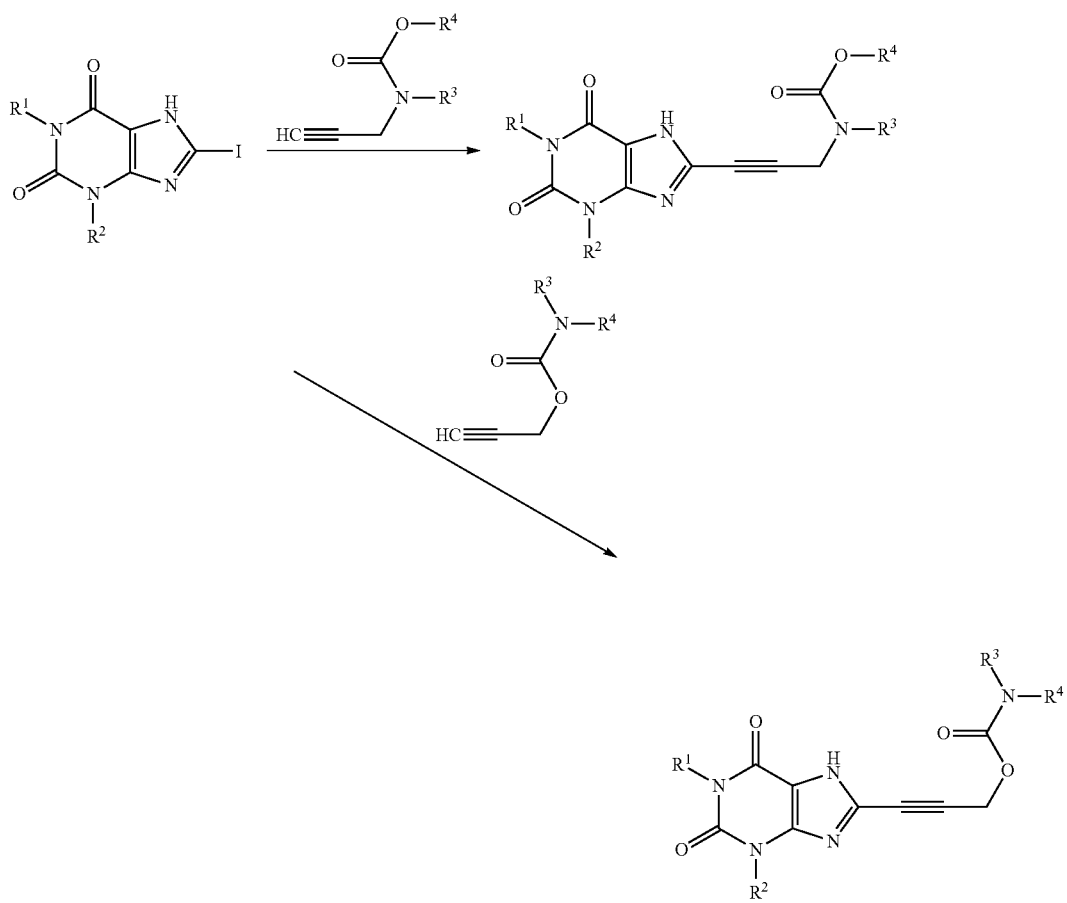

A solution of 1,3-dialkyl-8-iodoxanthine (1 equivalent), potassium carbonate (3.0 equivalents), copper(I) iodide (0.1 equivalents), palladium (0) tetrakistriphenylphosphine (0.1 equivalents) and alkyne (1.2 equivalents) in THF were stirred at 25° C. for at least 6 to 24 hrs. Silica bound Pd (II) scavenger Si-Thiol (4 mmole equivalents to Pd) and Pd (0) scavenger Si-TAAcOH (4 mmole equivalents to Pd) were added and stirring continued at 25° C. for an additional 24 hrs. The mixture was filtered, adhered to silica and purified by silica column chromatography. Like fractions were collected, and the solvent removed in vacuo to give product.

Example 1

1,3-Dicyclopropyl-8-(3-(methyl((4-fluorophenoxy) carbonyl)amino)prop-1-yn-1-yl)xanthine 1,3-Dicyclopropyl-8-iodoxanthine (115 mg, 0.32 mmole), copper (I) iodide (62 mg, 0.33 mmole), potassium carbonate (190 mg, 1.37 mmoles), THF (20 mL), palladium (0) tetrakistriphenylphosphine (70 mg, 0.061 mmole), and 4-fluorophenyl N-methyl-N-(prop-2-yn-1-yl)carbamate (147 mg, 0.71 mmole) were stirred at rt for 45 hr. Silica bound Pd(II) scavenger Si-Thiol (0.4 g) was added and stirred at rt for 72 hrs. Column chromatography (Si=14 g), eluting with MeOH (0-2%)/DCM to give 48 mg, 1.1 mmoles, 34% yield. HPLC-MS conditions: 20%-95% MeOH (0.1% formic acid)/H$_2$O (0.1% formic acid) 10 min. 10 min. hold, Rt=10.089, LRMS ESI (M+H$^+$) 438.35.

Example 2

1-Cyclopropyl-3-propyl-8-(3-(methyl((4-fluorophenoxy)carbonyl)amino)prop-1-yn-1-yl)xanthine 1-Cyclopropyl-3-propyl-8-iodoxanthine (103 mg, 0.29 mmole), copper (I) iodide (52 mg, 0.27 mmole), potassium carbonate (177 mg, 1.28 mmoles), THF (16 mL), DMF (2 mL), palladium (0) tetrakistriphenylphosphine (70 mg, 0.061 mmol), and 4-fluorophenyl N-methyl-N-(prop-2-yn-1-yl)carbamate (167 mg, 0.81 mmole) were stirred at rt for 46 hrs. An additional 75 mg of the alkyne was added and the mixture stirred for 4 hrs. Silica bound Pd(II) scavenger Si-Thiol (0.5 g) was added and stirred at rt for 55 hrs. Column chromatography (Si=26 g), eluting with methanol (0-3%)/DCM to give 59 mg, 0.134 mmole, 47% yield. HPLC-MS conditions: 20%-95% MeOH (0.1% formic acid)/H$_2$O (0.1% formic acid) 10 min. 10 min. hold, Rt=10.702, LRMS ESI (M+H$^+$) 440.30.

Example 3

1,3-Dicyclopropyl-8-(3-(methyl(phenoxycarbonyl) amino)prop-1-yn-1-yl)xanthine 1,3-Dicyclopropyl-8-iodoxanthine (58.2 mg, 0.163 mmole), potassium carbonate (0.095 g, 0.69 mmole), copper (I) iodide (35.6 mg, 0.187 mmole), palladium (0) tetrakistriphenylphosphine (48.0 mg, 0.068 mmole) and phenyl N-methyl-N-(prop-2-yn-1-yl)carbamate (0.121 g, 0.64 mmole) in THF (15 mL) was stirred at rt for 21 hrs. Silica bound Pd (II) scavenger Si-Thiol (0.25 g) and Pd (0) scavenger Si-TAAcOH (0.56 g) were added and stirring at rt continued a further for 24 hrs. Purified with silica plug with hexanes/ether then methanol/DCM and silica column chromatography (Si=14 g), eluting with methanol (0-0.5%)/DCM to give 33.7 mg, 0.034 mmole, 21% yield. HPLC-MS conditions: 20%-80% MeOH (0.1% formic acid)/H$_2$O (0.1% formic acid) 10 min. 10 min. hold, Rt=10.265, LRMS ESI (M+H$^+$) 420.30.

Example 4

1,3-Dicyclopropyl-8-(3-(methyl((3-(trifluoromethyl) phenoxy)carbonyl)-amino)prop-1-yn-1-yl)xanthine 1,3-Dicyclopropyl-8-iodoxanthine (63.0 mg, 0.18 mmole), potassium carbonate (0.105 g, 0.76 mmole), copper (I) iodide (62.5 mg, 0.33 mmole), palladium (0) tetrakistriphenylphosphine (69.0 mg, 0.098 mmole) and 3-(trifluoromethyl)phenyl N-methyl-N-(prop-2-yn-1-yl)carbamate (0.167 g, 0.65 mmole) in THF (15 mL) was stirred at rt for 21 hrs. Silica bound Pd (II) scavenger Si-Thiol (0.33 g) and Pd (0) scavenger Si-TAAcOH (0.79 g) were added and stirring at rt continued a further for 47 hrs. Purified by silica column chromatography (silica=14 g), eluting with methanol (0-1%)/DCM to give 11 mg, 0.023 mmole, 13% yield. HPLC-MS conditions: 20%-95% MeOH (0.1% formic acid)/H$_2$O (0.1% formic acid) 10 min. 10 min. hold, Rt=11.009, LRMS ESI (M+H$^+$) 488.35.

Example 5

1,3-Dicyclopropyl-8-(3-(methyl((2-methoxyphenoxy)carbonyl)amino)prop-1-yn-1-yl)xanthine 1,3-Dicyclopropyl-8-iodoxanthine (203 mg, 0.57 mmole), copper (I) iodide (135 mg, 0.71 mmole), potassium carbonate (352 mg, 2.55 mmole), palladium (0) tetrakistriphenylphosphine (154 mg, 0.13 mmole), 2-methoxyphenyl N-methyl-N-(prop-2-yn-1-yl)carbamate (335 mg, 1.53 mmole), in THF (30 mL) was stirred at rt for 70 hrs. Silica bound Pd(II) scavenger Si-Thiol (0.8 g) was added and stirring at rt continued a further 72 hrs. Purified by silica column chromatography (Si=14 g), eluting with methanol (0-3%)/DCM to give 95 mg, 0.21 mmole, 37% yield. HPLC-MS conditions: 20%-95% MeOH (0.1% formic acid)/H$_2$O (0.1% formic acid) 10 min. 10 min. hold, Rt=10.075, LRMS ESI (M+H$^+$) 450.20.

Example 6

8-(3-(((2-Chlorophenoxy)carbonyl)(methyl)amino) prop-1-yn-1-yl)-1,3-dicyclopropylxanthine 1,3-Dicyclopropyl-8-iodoxanthine (71.8 mg, 0.20 mmole), potassium carbonate (0.12 g, 0.84 mmole), copper (I) iodide (40.5 mg, 0.21 mmole), palladium (0) tetrakistriphenylphosphine (58.0 mg, 0.083 mmole) and 2-chlorophenyl N-methyl-N-(prop-2-yn-1-yl)carbamate (0.128 g, 0.57 mmole) in THF (15 mL) was stirred at rt for 44 hrs. Silica bound Pd (II) scavenger Si-Thiol (0.29 g) and Pd (0) scavenger Si-TAAcOH (0.67 g) were added and stirring at rt continued a further 25 hrs. Purified by silica column chromatography (Si=14 g), eluting with methanol (0-0.5%)/DCM and again by silica column chromatography (Si=14 g), eluting with methanol (0-3%)/DCM to give 14 mg, 0.031 mmole, 15% yield. HPLC-MS conditions: 20%-95% MeOH (0.1% formic acid)/H$_2$O (0.1% formic acid) 10 min. 10 min. hold, Rt=10.627, LRMS ESI (M+H$^+$) 454.30.

Example 7

1,3-Dicyclopropyl-8-(3-((methyl(phenyl)carbamoyl)oxy)prop-1-yn-1-yl)xanthine 1,3-Dicyclopropyl-8-iodoxanthine (64.8 mg, 0.18 mmole), potassium carbonate (0.11 g, 0.8046 mmole), copper(I) iodide (41.0 mg, 0.22 mmole), palladium (0) tetrakistriphenylphosphine (65.0 mg, 0.093 mmole), and prop-2-yn-1-yl methyl(phenyl)carbamate (0.11 g, 0.587 mmole) in THF (15 mL) was stirred at rt for 24 hrs. Additional prop-2-yn-1-yl N-methyl-N-phenylcarbamate (0.09 g, 0.48 mmole) was added and stirring continued for 19 hrs. Silica bound Pd (II) scavenger Si-Thiol (0.299 g) and Pd (0) scavenger Si-TAAcOH (0.740 g) were added and stirring at rt continued a further 6 days. Purified by silica column chromatography (Si=14 g), eluting with methanol (0-3%)/DCM to give 36 mg, 0.085 mmole, 47% yield. HPLC-MS conditions: 40%-80% MeOH (0.1% formic acid)/$H_2O$ (0.1% formic acid) 10 min. 5 min. hold, Rt=10.395, LRMS ESI (M+H$^+$) 420.30.

Example 8

8-(3-(((4-Chlorophenyl)(methyl)carbamoyl)oxy)prop-1-yn-1-yl)-1,3-dicyclopropylxanthine 1,3-Dicyclopropyl-8-iodoxanthine (85.6 mg, 0.24 mmole), potassium carbonate (0.1607 g, 1.16 mmole), copper(I) iodide (42.4 mg, 0.22 mmole), palladium (0) tetrakistriphenylphosphine (67.0 mg, 0.096 mmole), prop-2-yn-1-yl N-4-chlorophenyl-N-methylcarbamate (0.127 g, 0.57 mmole) in THF (15 mL) was stirred at rt for 21.5 hrs. Silica bound Pd (II) scavenger Si-Thiol (0.339 g) and Pd (0) scavenger Si-TAAcOH (0.755 g) were added and stirring at rt continued for 27 hrs. Purified by silica column chromatography (silica=14 g), eluting with methanol (0-0.5%)/DCM and again by silica column chromatography (Si=14 g), eluting with methanol (0-2%)/DCM to give 8 mg, 0.02 mmole, 7% yield. HPLC-MS conditions: 20%-95% MeOH (0.1% formic acid)/$H_2O$ (0.1% formic acid) 10 min. 10 min. hold, Rt=10.500, LRMS ESI (M+H$^+$) 454.10.

Representative compounds of the present invention have been tested for their activity as $A_{2B}$ antagonists and shown to be active. For example, the binding of percent inhibition at $1\times10^{-7}$M values for tested compounds is provided in Table 1. These values were obtained by using the following methodology.

The cells are suspended in HBSS buffer (Invitrogen) complemented with 20 mM HEPES (pH 7.4), then distributed in microplates at a density of $5\times10^3$ cells/well and preincubated for 5 min at room temperature in the presence of HBSS (basal control), the test compound or the reference antagonist. Thereafter, the reference agonist NECA is added at a final concentration of 1 μM. For basal control measurements, separate assay wells do not contain NECA. Following 10 min incubation at 37° C., the cells are lysed and the fluorescence acceptor (D2-labeled cAMP) and fluorescence donor (anti-cAMP antibody labeled with europium cryptate) are added. After 60 min at room temperature, the fluorescence transfer is measured at λex=337 nm and λem=620 and 665 nm using a microplate reader (Rubystar, BMG). The cAMP concentration is determined by dividing the signal measured at 665 nm by that measured at 620 nm (ratio). The results are expressed as a percent inhibition of the control response to 1 μM NECA. The standard reference antagonist is XAC, which is tested in each experiment at several concentrations to generate a concentration-response curve from which its IC50 value is calculated.

Reference: Cooper, J., Hill, S. J., and Alexander, S. P. H. (1997), An endogenous $A_2B$ adenosine receptor coupled to cyclic AMP generation in human embryonic kidney (HEK-293) cells, Brit. J. Pharmacol., 122: 546.

TABLE 1

| Ex # | Structure | % Inhibition |
|---|---|---|
| 1 | 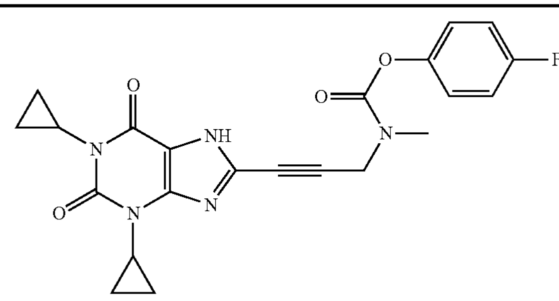 | ++ |
| 2 | 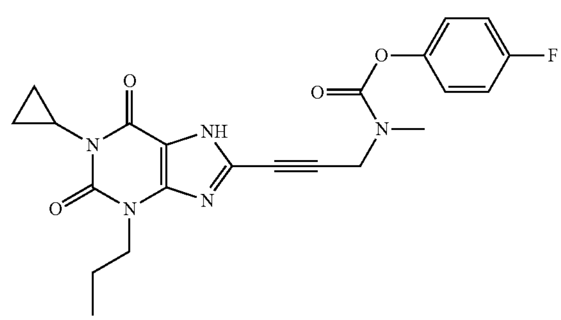 [SMILES: CCCn1c(=O)n(C2CC2)c(=O)c2[nH]c(C#CCN(C)C(=O)Oc3ccc(F)cc3)nc21] | ++ |

TABLE 1-continued

| Ex # | Structure | % Inhibition |
|------|-----------|--------------|
| 3 | (1,3-dicyclopropyl-xanthine with 8-propargyl-N-methyl-N-(phenoxycarbonyl)amine substituent) | + |
| 4 | (1,3-dicyclopropyl-xanthine with 8-propargyl-N-methyl-N-(3-trifluoromethylphenoxycarbonyl)amine substituent) | + |
| 5 | (1,3-dicyclopropyl-xanthine with 8-propargyl-N-methyl-N-(2-methoxyphenoxycarbonyl)amine substituent) | + |
| 6 | (1,3-dicyclopropyl-xanthine with 8-propargyl-N-methyl-N-(2-chlorophenoxycarbonyl)amine substituent) | + |
| 7 | (1,3-dicyclopropyl-xanthine with 8-propargyloxycarbonyl-N-methyl-N-(4-chlorophenyl)amine substituent) | + |

TABLE 1-continued

| Ex # | Structure | % Inhibition |
|------|-----------|--------------|
| 8 | 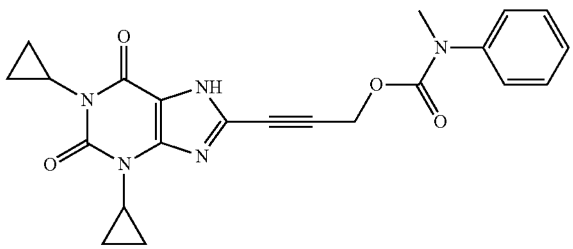 [SMILES: CN(C(=O)OCC#Cc1nc2c([nH]1)c(=O)n(C1CC1)c(=O)n2C1CC1)c1ccccc1] | ++ |

+ >5%
++ >20%

Examples 1-46 of Tables 2A-B are additional representative examples of the present invention. These examples can be synthesized using the methods described above by coupling the corresponding methyl/ethyl/cyclopropyl-uronamide and corresponding 2-substituted-propyn-1-yl. The starting 2-substituted-propyn-1-yl groups can be prepared according to the general procedures provided above.

TABLE 2A

| Ex # | Structure |
|------|-----------|
| 1. | 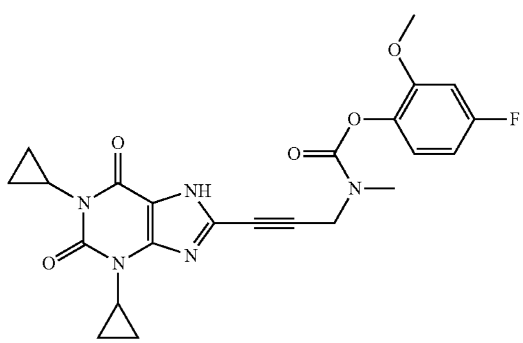 [SMILES: COc1cc(F)ccc1OC(=O)N(C)CC#Cc1nc2c([nH]1)c(=O)n(C1CC1)c(=O)n2C1CC1] |
| 2. | 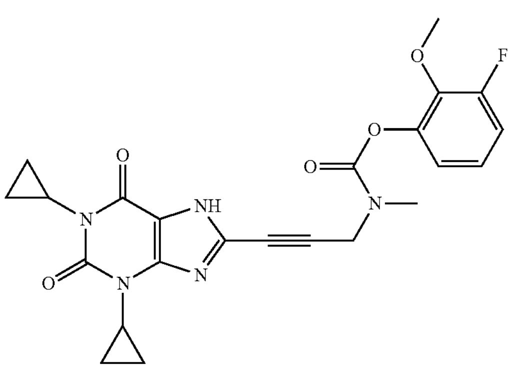 [SMILES: COc1c(F)cccc1OC(=O)N(C)CC#Cc1nc2c([nH]1)c(=O)n(C1CC1)c(=O)n2C1CC1] |

TABLE 2A-continued

| Ex # | Structure |
|------|-----------|
| 3. | 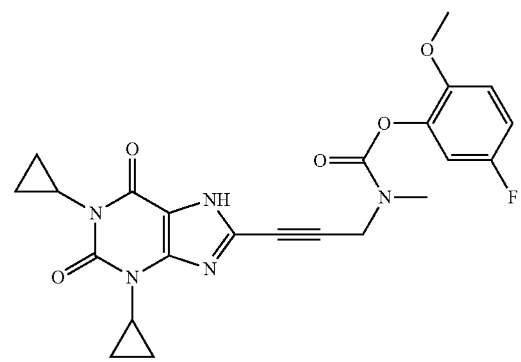 [SMILES: COc1ccc(F)cc1OC(=O)N(C)CC#Cc1nc2c([nH]1)c(=O)n(C1CC1)c(=O)n2C1CC1] |
| 4. | 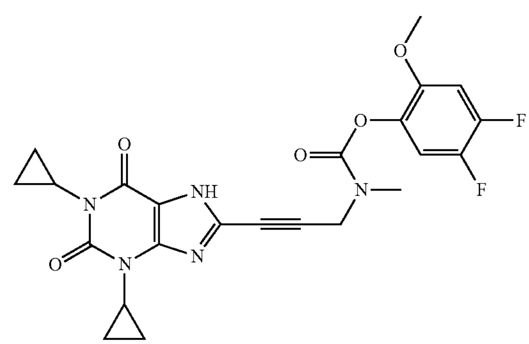 [SMILES: COc1cc(F)c(F)cc1OC(=O)N(C)CC#Cc1nc2c([nH]1)c(=O)n(C1CC1)c(=O)n2C1CC1] |
| 5. | 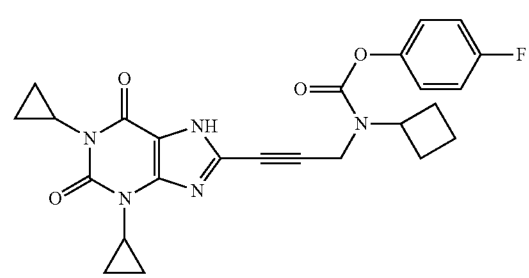 [SMILES: O=C(Oc1ccc(F)cc1)N(CC#Cc1nc2c([nH]1)c(=O)n(C1CC1)c(=O)n2C1CC1)C1CCC1] |

TABLE 2A-continued

| Ex # | Structure |
|---|---|
| 6. | 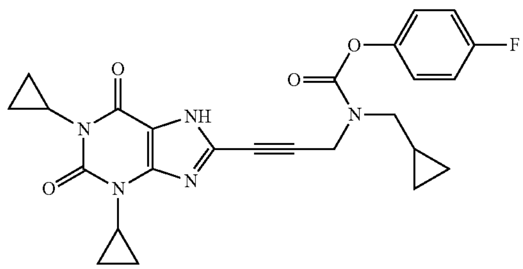 [SMILES: O=C(Oc1ccc(F)cc1)N(CC#Cc1nc2c([nH]1)c(=O)n(C1CC1)c(=O)n2C1CC1)CC1CC1] |
| 7. | 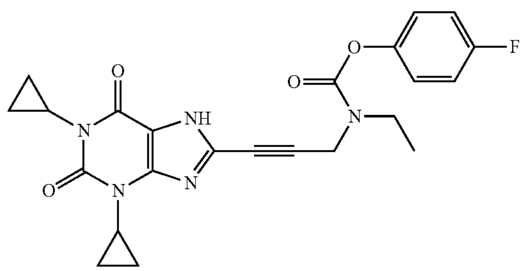 [SMILES: CCN(CC#Cc1nc2c([nH]1)c(=O)n(C1CC1)c(=O)n2C1CC1)C(=O)Oc1ccc(F)cc1] |
| 8. | 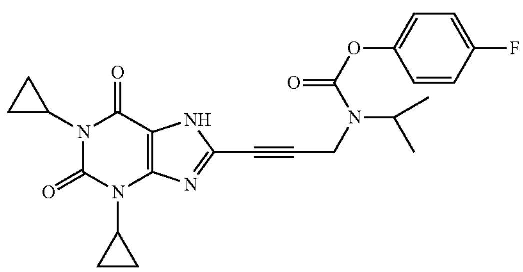 [SMILES: CC(C)N(CC#Cc1nc2c([nH]1)c(=O)n(C1CC1)c(=O)n2C1CC1)C(=O)Oc1ccc(F)cc1] |
| 9. | 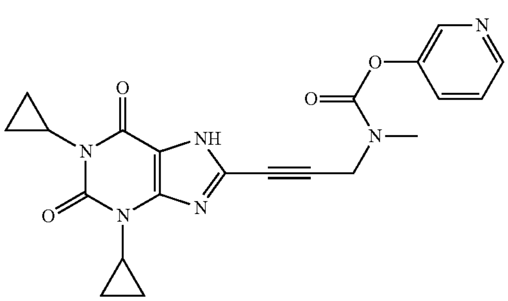 [SMILES: CN(CC#Cc1nc2c([nH]1)c(=O)n(C1CC1)c(=O)n2C1CC1)C(=O)Oc1cccnc1] |
| 10. | 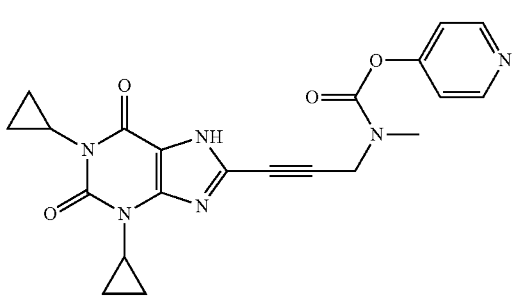 [SMILES: CN(CC#Cc1nc2c([nH]1)c(=O)n(C1CC1)c(=O)n2C1CC1)C(=O)Oc1ccncc1] |
| 11. | |
| 12. | |
| 13. | |
| 14. | |
| 15. | |

TABLE 2A-continued
| Ex # | Structure |
|---|---|
| 16. | 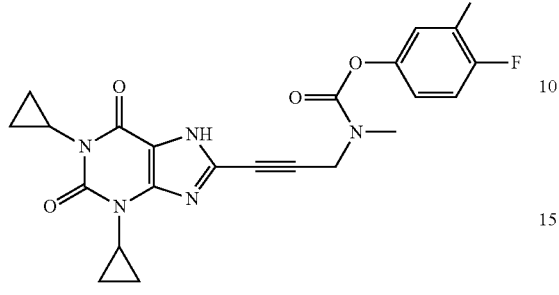 |
| 17. | 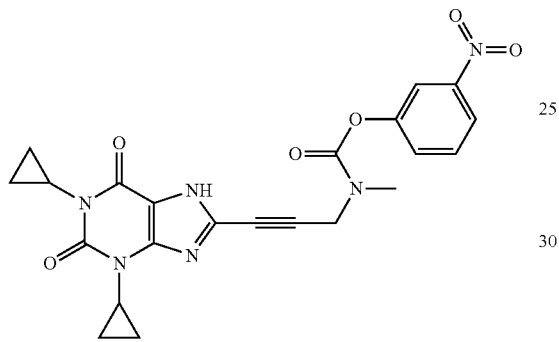 |
| 18. | 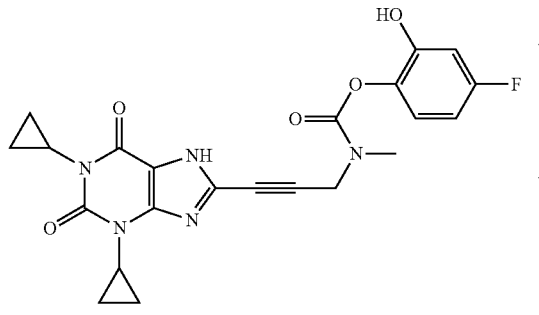 |
| 19. | 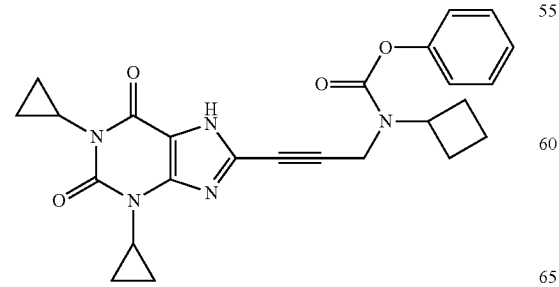 |
| 21. | 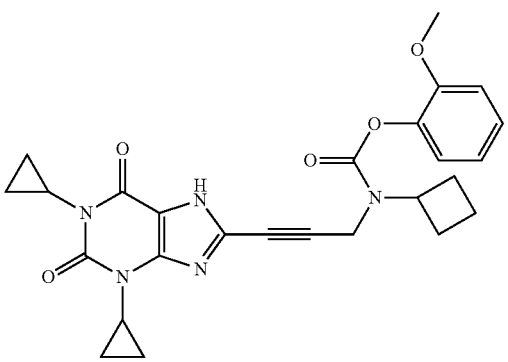 |
| 22. | 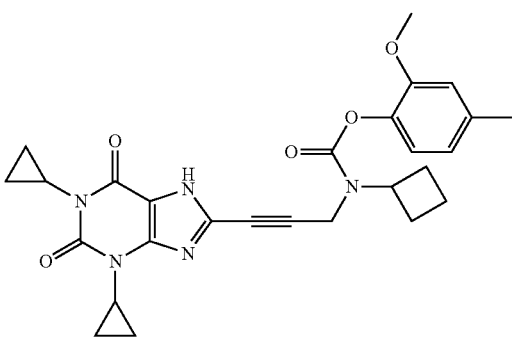 |
| 23. | 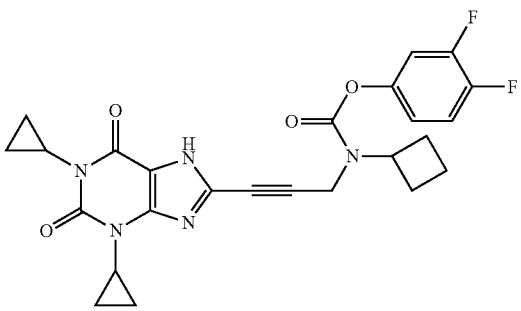 |
| 24. | 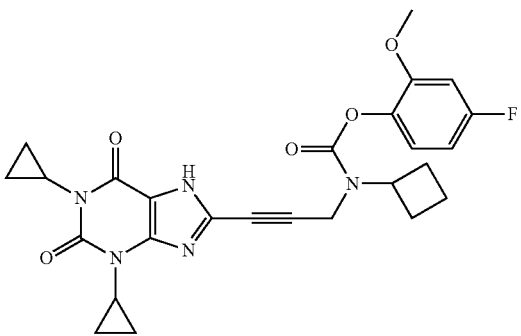 |

TABLE 2A-continued
| Ex # | Structure |
|---|---|
| 25. | 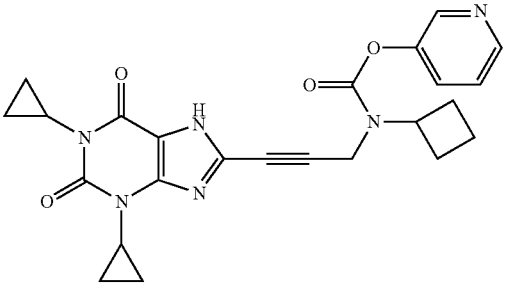 |
| 26. | 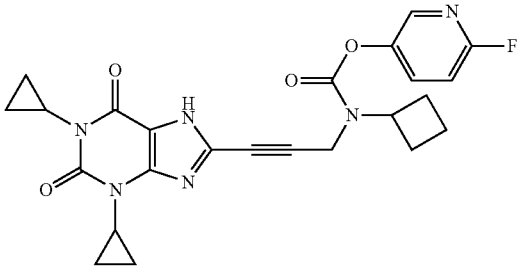 |
| 27. | 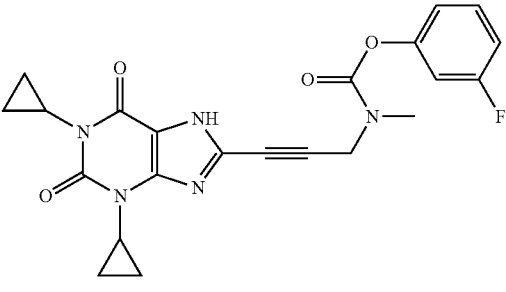 |
| 28. | 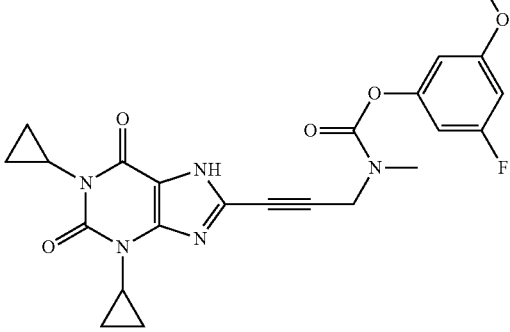 |
| 29. | 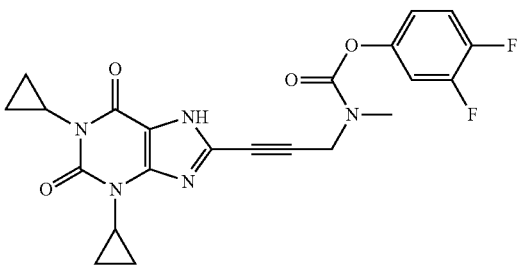 |
| 30. | 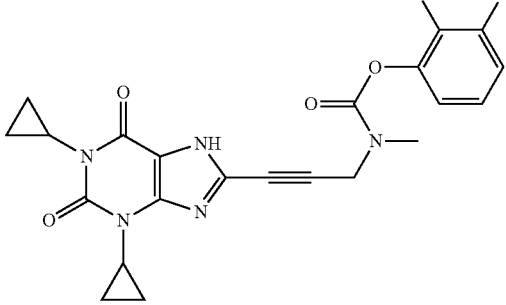 |
| 31. | 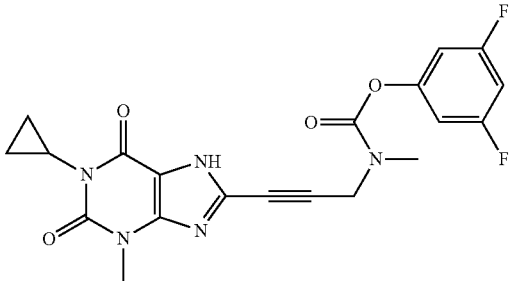 |
| 32. | 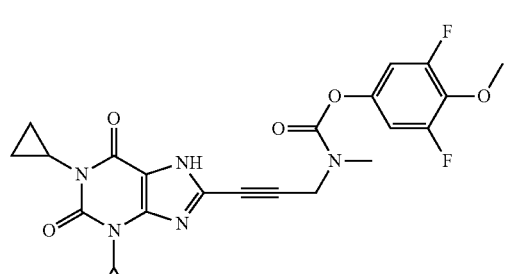 |
| 33. | 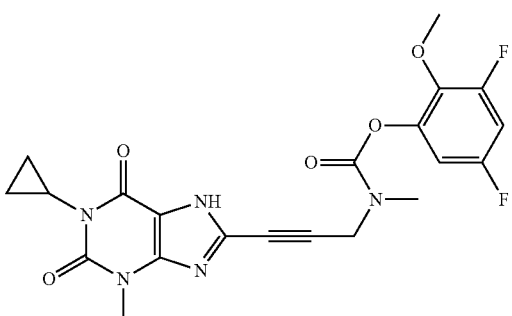 |
| 34. | 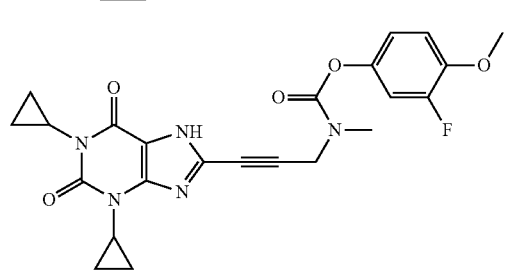 |

TABLE 2B

| Ex # | Structure |
|---|---|
| 35. | 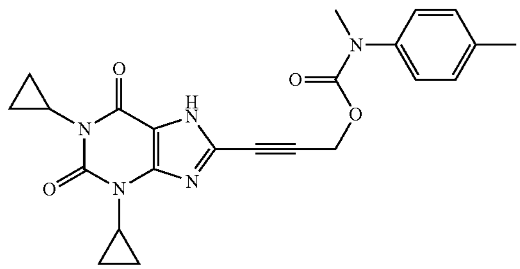 |
| 36. | 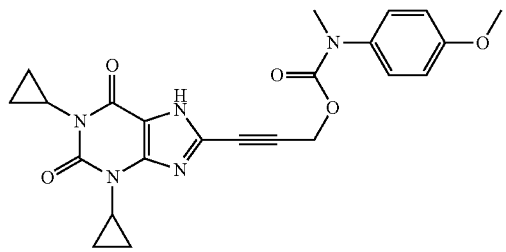 |
| 37. | 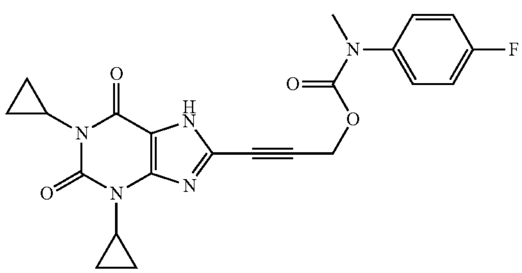 |
| 38. | 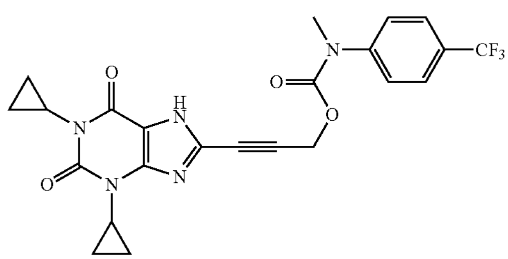 |
| 39. | 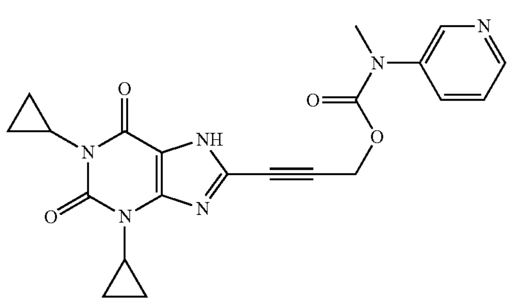 |
| 40. | |
| 41. | |
| 42. | |
| 43. | |

TABLE 2B-continued

| Ex # | Structure |
|---|---|
| 44. | 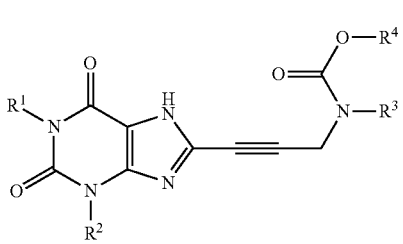 |
| 45. | 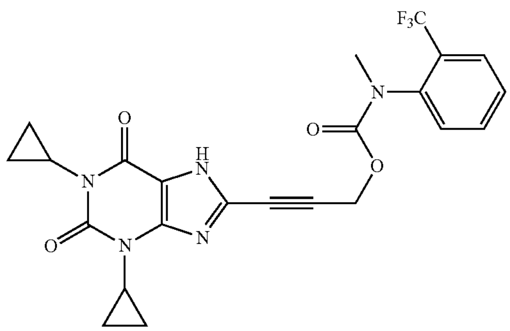 |
| 46. | 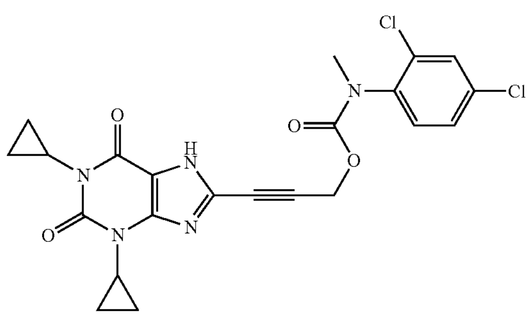 |

All references listed herein are individually incorporated in their entirety by reference.

Numerous modifications and variations of the present invention are possible in light of the above teachings. It is therefore to be understood that within the scope of the appended claims, the invention may be practiced otherwise than as specifically described herein.

What is claimed is:

1. A compound of Formula I or II or a stereoisomer or pharmaceutically acceptable salt thereof:

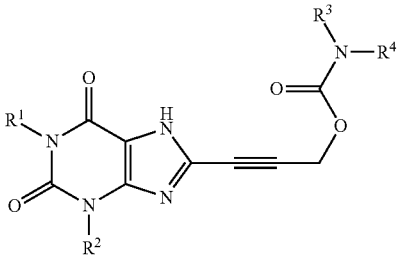

wherein:
R$^1$ is selected from: C$_{1-5}$ alkyl, —C$_{2-5}$ alkylene-OH, —C$_{2-5}$ alkylene-O—C$_{1-5}$ alkyl, C$_{3-6}$ cycloalkyl, —C$_{1-3}$ alkylene-C$_{3-6}$ cycloalkyl, —CH$_2$—C$_{2-4}$ alkenyl, —CH$_2$—C$_{2-4}$ alkynyl, and —C$_{3-6}$ cycloalkylene-O—C$_{1-3}$ alkyl;

R$^2$ is selected from: C$_{1-5}$ alkyl, —C$_{2-5}$ alkylene-OH, —C$_{2-5}$ alkylene-O—C$_{1-5}$ alkyl, C$_{3-6}$ cycloalkyl, —C$_{1-3}$ alkylene-C$_{3-6}$ cycloalkyl, —CH$_2$—C$_{2-4}$ alkenyl, —CH$_2$—C$_{2-4}$ alkynyl, and —C$_{3-6}$ cycloalkylene-O—C$_{1-3}$ alkyl;

R$^3$ is selected from: C$_{1-6}$ alkyl, —C$_{2-5}$ alkylene-O—C$_{1-5}$ alkyl, —C$_{2-5}$ alkylene-S—C$_{1-5}$ alkyl, —C$_{2-5}$ alkylene-NR$^a$R$^b$, —C$_{2-5}$ alkylene-OH, —C$_{2-5}$ alkylene-SH, —C$_{2-5}$ alkylene-NR$^a$R$^b$, C$_{3-6}$ cycloalkyl, and, —C$_{1-3}$ alkylene-C$_{3-6}$ cycloalkyl;

R$^4$ is selected from: phenyl and 5-6 membered heteroaryl; the phenyl and heteroaryl groups of R$^4$ are optionally substituted with 1-3 groups independently selected from: C$_{1-4}$ alkyl, C$_{3-6}$ cycloalkyl, —C$_{1-3}$ alkylene-C$_{3-6}$ cycloalkyl, F, Cl, Br, I, —CN, OR$^a$, SR$^a$, NR$^a$R$^b$, CF$_3$, OCF$_3$, COR$^a$, CO$_2$R$^a$, C(O)NR$^a$R$^b$, OC(O)R$^a$, OCO$_2$R$^a$, OC(O)NR$^a$R$^b$, NR$^b$COR$^a$, NR$^b$CO$_2$R$^a$, NR$^b$-C(O)NR$^a$R$^b$, and S(O)$_p$NR$^a$R$^b$;

each R$^a$ is independently selected from: H, C$_{1-8}$ alkyl, C$_{3-6}$ cycloalkyl, and —C$_{1-3}$ alkylene-C$_{3-6}$ cycloalkyl;

each R$^b$ is independently selected from: H, C$_{1-8}$ alkyl, C$_{3-6}$ cycloalkyl, and —C$_{1-3}$ alkylene-C$_{3-6}$ cycloalkyl;

alternatively, each NR$^a$R$^b$ group is optionally selected from a 3-6 membered cyclic amine; and, p is independently selected from: 0, 1, and 2.

2. A compound of claim 1, wherein the compound is of Formula I or a stereoisomer or pharmaceutically acceptable salt thereof.

3. A compound of claim 2, wherein:
R$^1$ is selected from: C$_{1-3}$ alkyl and C$_{3-6}$ cycloalkyl;
R$^2$ is selected from: C$_{1-3}$ alkyl and C$_{3-6}$ cycloalkyl;
R$^3$ is selected from: C$_{1-6}$ alkyl and —C$_{1-3}$ alkylene-C$_{3-6}$ cycloalkyl;
R$^4$ is selected from: phenyl and 5-6 membered heteroaryl; the phenyl and heteroaryl groups of R$^4$ are optionally substituted with 1-2 groups independently selected from: C$_{1-4}$ alkyl, C$_{3-6}$ cycloalkyl, —C$_{1-3}$ alkylene-C$_{3-6}$ cycloalkyl, F, Cl, Br, I, —CN, OR$^a$, SR$^a$, NR$^a$R$^b$, CF$_3$, OCF$_3$, COR$^a$, CO$_2$R$^a$, C(O)NR$^a$R$^b$, OC(O)R$^a$, OCO$_2$R$^a$, OC(O)NR$^a$R$^b$, NR$^b$COR$^a$, NR$^b$CO$_2$R$^a$, NR$^b$-C(O)NR$^a$R$^b$, and S(O)$_p$NR$^a$R$^b$;

each R$^a$ is independently selected from: H, C$_{1-4}$ alkyl, C$_{3-6}$ cycloalkyl, and —C$_{1-3}$ alkylene-C$_{3-6}$ cycloalkyl;

each R$^b$ is independently selected from: H, C$_{1-4}$ alkyl, C$_{3-6}$ cycloalkyl, and —C$_{1-3}$ alkylene-C$_{3-6}$ cycloalkyl; and, p is independently selected from: 0, 1, and 2.

4. A compound of claim 3, wherein:

ring $R^4$ is selected from phenyl, pyridyl, thienyl, furanyl, pyrrolyl, oxazolyl, isoxazolyl, thiazolyl, isothiazolyl, pyrimidyl, and pyridazinyl.

5. A compound of claim 4, wherein:

ring $R^4$ is selected from phenyl and pyridyl.

6. A compound of claim 5, wherein:

$R^1$ is selected from: methyl, ethyl, and cyclopropyl;

$R^2$ is selected from: methyl, ethyl, and cyclopropyl;

$R^3$ is selected from: methyl, ethyl, and -methylene-cyclopropyl;

$R^4$ is phenyl optionally substituted with 1-2 groups independently selected from: $C_{1-4}$ alkyl, $C_{3-6}$ cycloalkyl, —$C_{1-3}$ alkylene-$C_{3-6}$ cycloalkyl, F, Cl, —CN, $OR^a$, $NR^aR^b$, $CF_3$, and $OCF_3$;

each $R^a$ is independently selected from: H, methyl, and ethyl; and, each $R^b$ is independently selected from: H, methyl, and ethyl.

7. A compound of claim 1, wherein the compound is selected from compounds 1-6:

1

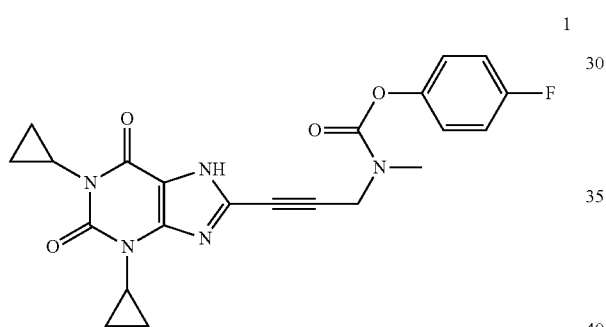

2

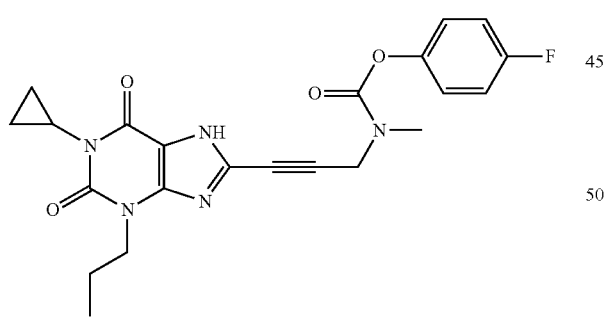

3

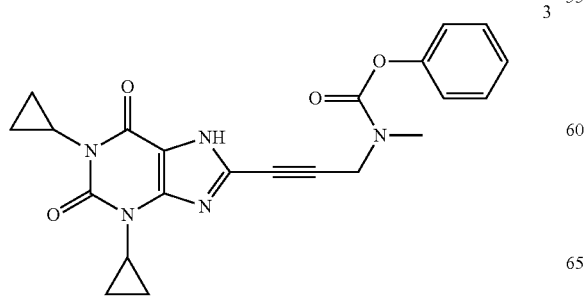

4

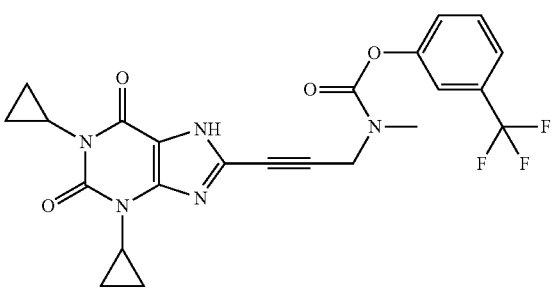

5

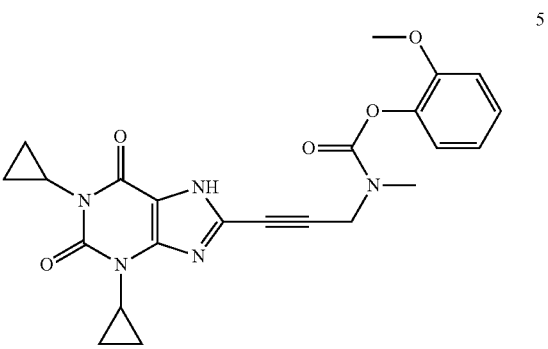

6

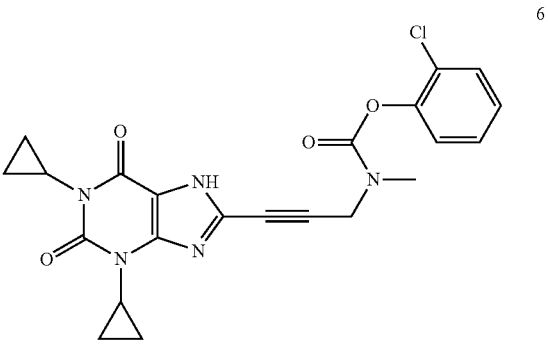

or a pharmaceutically acceptable salt thereof.

8. A compound of claim 1, wherein the compound is selected from compounds 1-26:

1

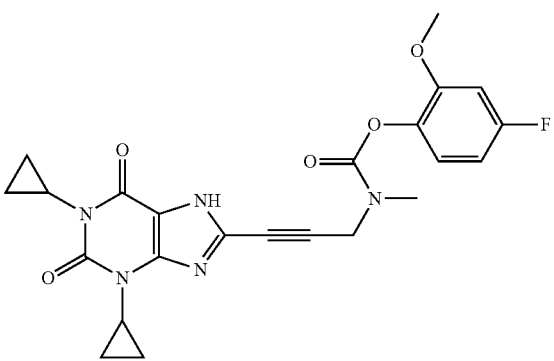

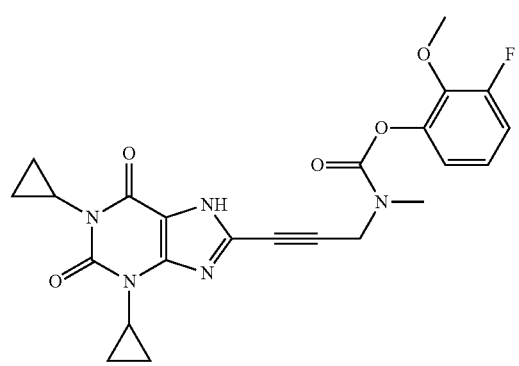
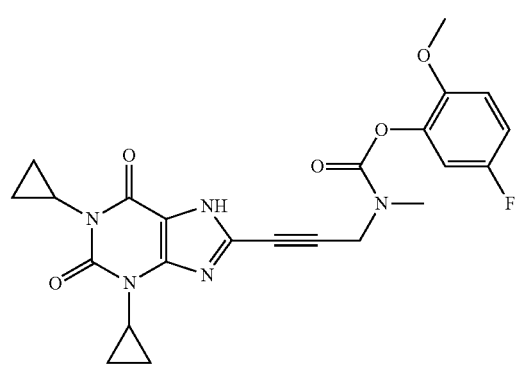
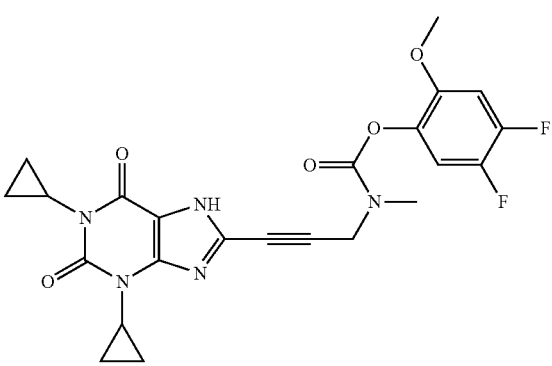
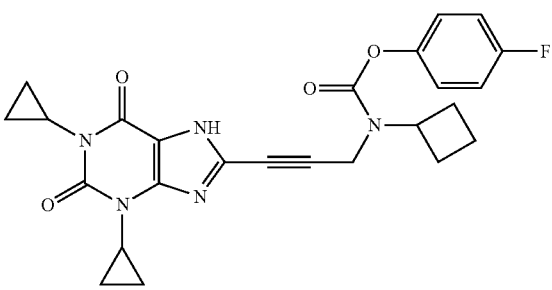
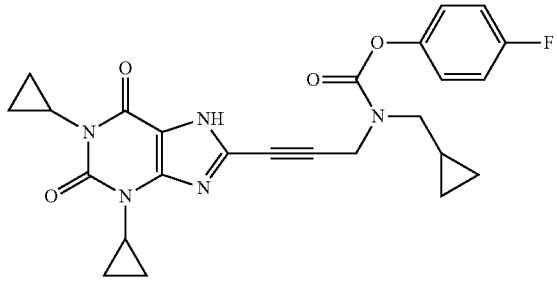
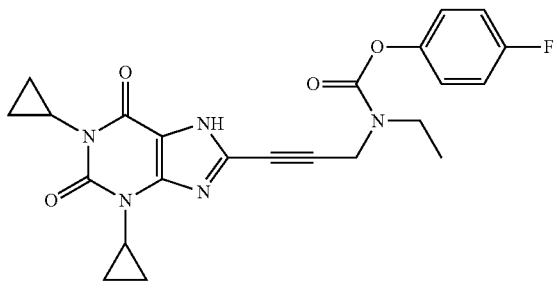
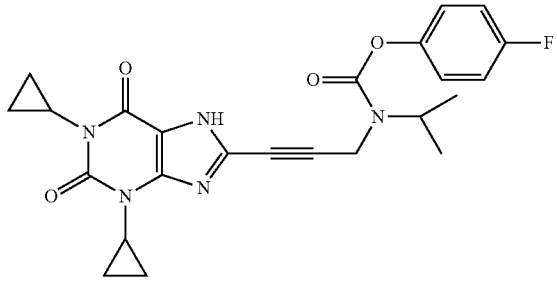
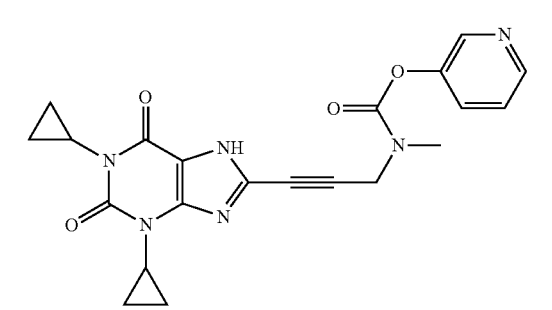
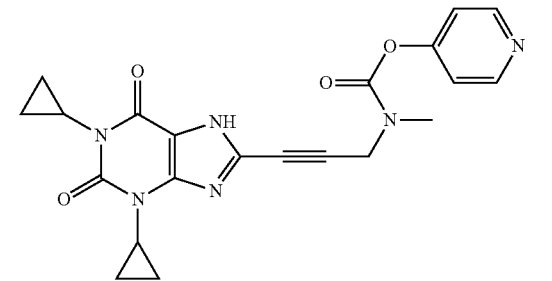

11
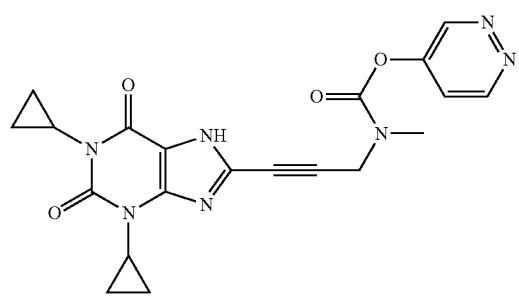 [SMILES: CN(CC#Cc1nc2c([nH]1)c(=O)n(C1CC1)c(=O)n2C1CC1)C(=O)Oc1ccnnc1]
12
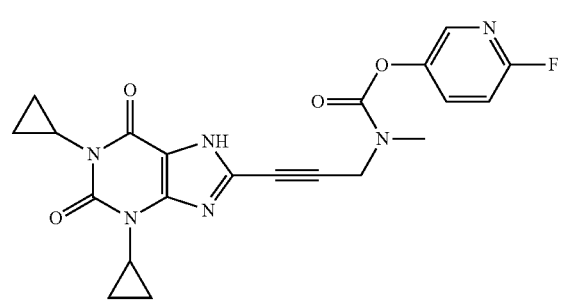 [SMILES: CN(CC#Cc1nc2c([nH]1)c(=O)n(C1CC1)c(=O)n2C1CC1)C(=O)Oc1ccc(F)nc1]
13
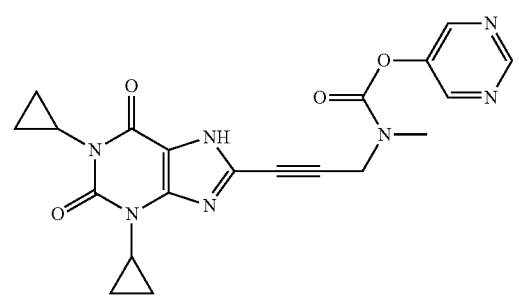 [SMILES: CN(CC#Cc1nc2c([nH]1)c(=O)n(C1CC1)c(=O)n2C1CC1)C(=O)Oc1cncnc1]
14
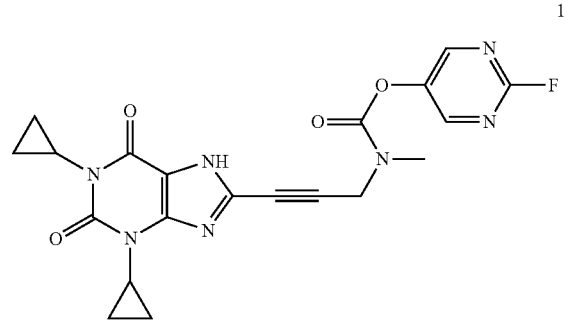
15
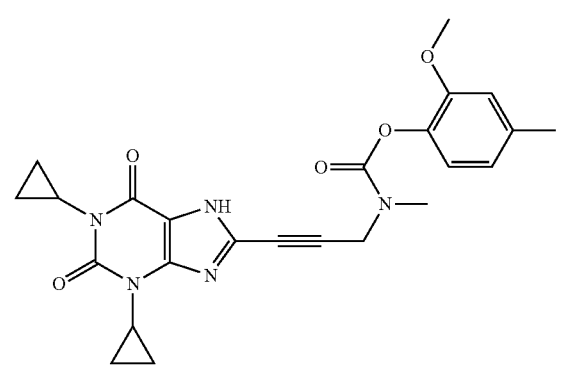 [SMILES: COc1cc(C)ccc1OC(=O)N(C)CC#Cc1nc2c([nH]1)c(=O)n(C1CC1)c(=O)n2C1CC1]
16
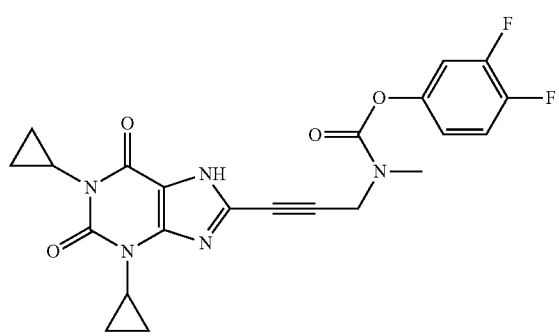 [SMILES: CN(CC#Cc1nc2c([nH]1)c(=O)n(C1CC1)c(=O)n2C1CC1)C(=O)Oc1ccc(F)c(F)c1]
17
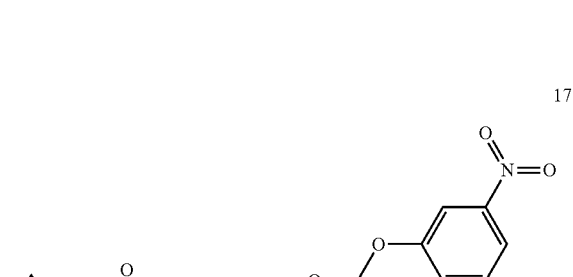
18
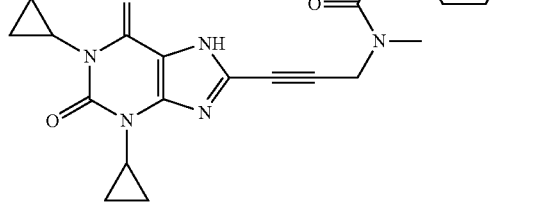
19
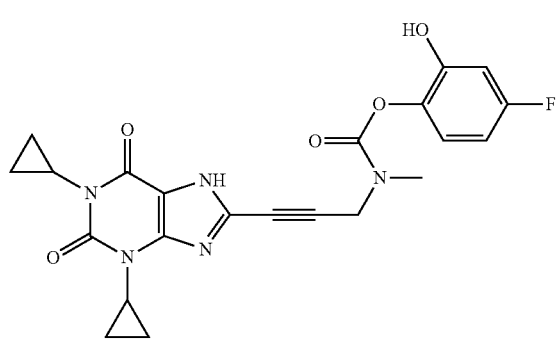 [SMILES: CN(CC#Cc1nc2c([nH]1)c(=O)n(C1CC1)c(=O)n2C1CC1)C(=O)Oc1ccc(F)cc1O]

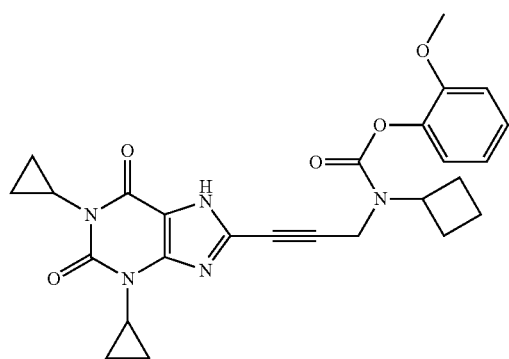 [SMILES: COc1ccccc1OC(=O)N(CC#Cc1nc2c([nH]1)c(=O)n(C1CC1)c(=O)n2C1CC1)C1CCC1]
21
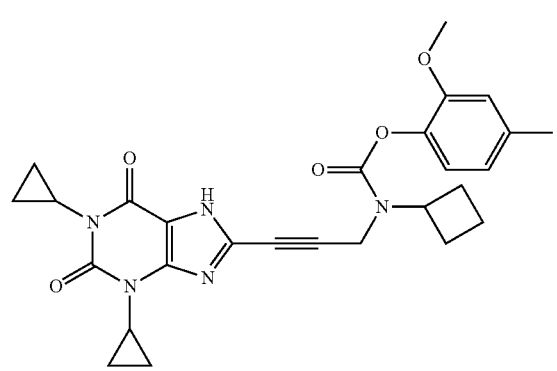 [SMILES: COc1cc(C)ccc1OC(=O)N(CC#Cc1nc2c([nH]1)c(=O)n(C1CC1)c(=O)n2C1CC1)C1CCC1]
22
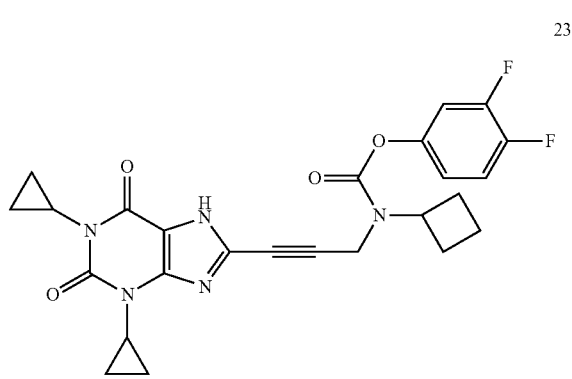
23
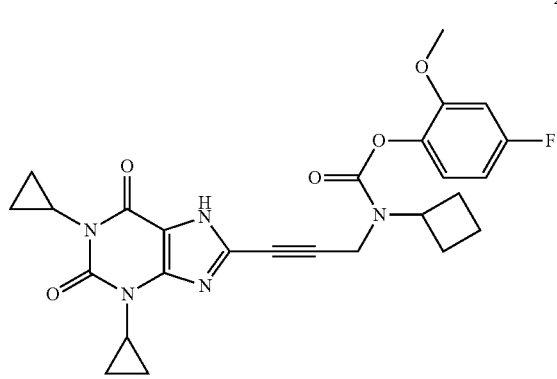
24
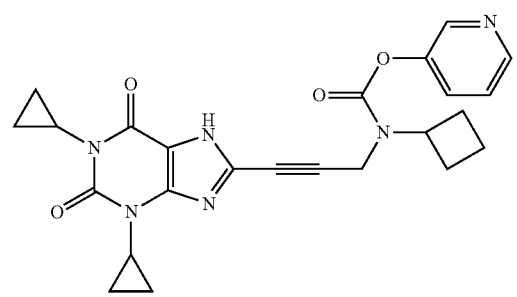 [SMILES: O=C(Oc1cccnc1)N(CC#Cc1nc2c([nH]1)c(=O)n(C1CC1)c(=O)n2C1CC1)C1CCC1]
25
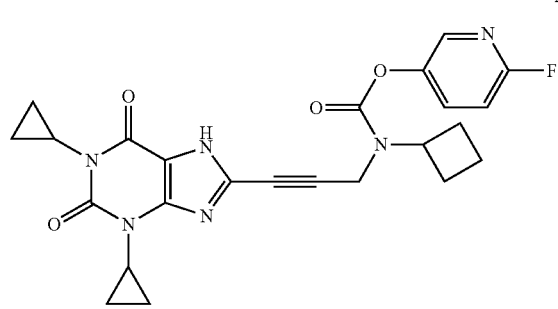
26
or pharmaceutically acceptable salt thereof.
9. A compound of claim 1, wherein the compound is selected from compounds 27-34:
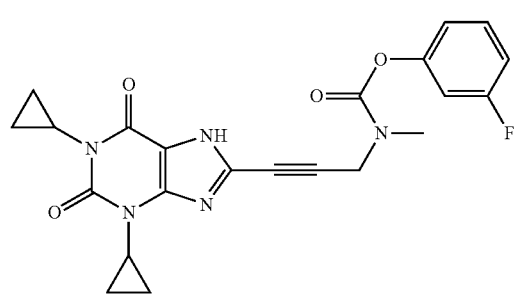 [SMILES: CN(CC#Cc1nc2c([nH]1)c(=O)n(C1CC1)c(=O)n2C1CC1)C(=O)Oc1cccc(F)c1]
27
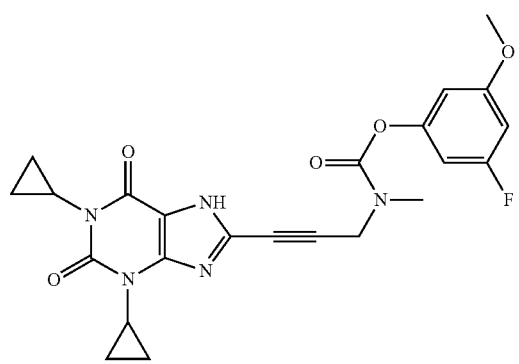 [SMILES: COc1cc(F)cc(OC(=O)N(C)CC#Cc2nc3c([nH]2)c(=O)n(C2CC2)c(=O)n3C2CC2)c1]
28

-continued

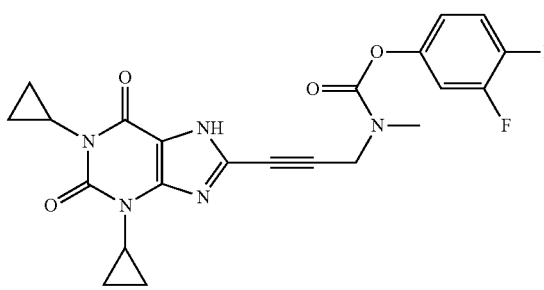

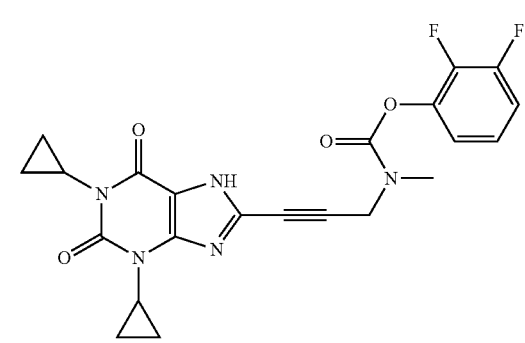 [SMILES: CN(CC#Cc1nc2c([nH]1)c(=O)n(C1CC1)c(=O)n2C1CC1)C(=O)Oc1cccc(F)c1F]

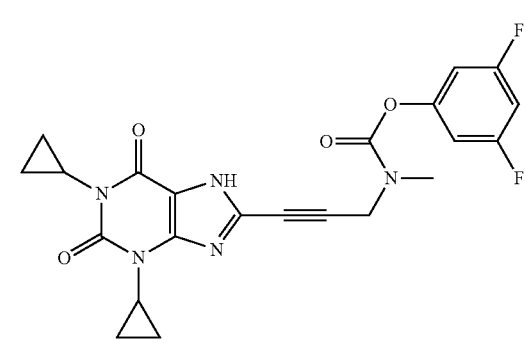 [SMILES: CN(CC#Cc1nc2c([nH]1)c(=O)n(C1CC1)c(=O)n2C1CC1)C(=O)Oc1cc(F)cc(F)c1]

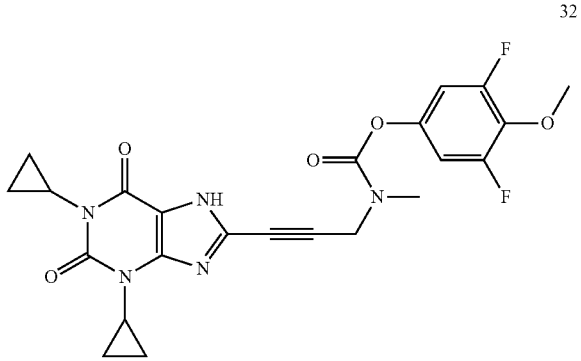

-continued

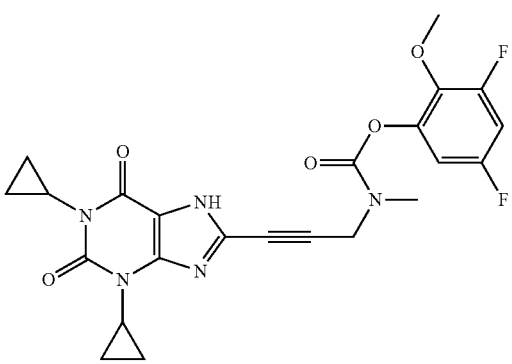 [SMILES: COc1c(F)cc(F)cc1OC(=O)N(C)CC#Cc1nc2c([nH]1)c(=O)n(C1CC1)c(=O)n2C1CC1]

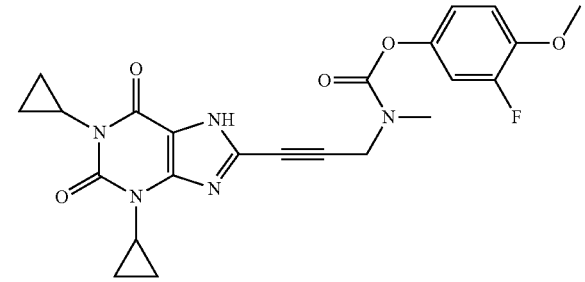 [SMILES: COc1ccc(OC(=O)N(C)CC#Cc2nc3c([nH]2)c(=O)n(C2CC2)c(=O)n3C2CC2)cc1F]

or pharmaceutically acceptable salt thereof.

10. A compound of claim 1, wherein the compound is of Formula II or a stereoisomer or pharmaceutically acceptable salt thereof.

11. A compound of claim 10, wherein:
$R^1$ is selected from: $C_{1-3}$ alkyl and $C_{3-6}$ cycloalkyl;
$R^2$ is selected from: $C_{1-3}$ alkyl and $C_{3-6}$ cycloalkyl;
$R^3$ is selected from: $C_{1-6}$ alkyl and —$C_{1-3}$ alkylene-$C_{3-6}$ cycloalkyl;
$R^4$ is selected from: phenyl and 5-6 membered heteroaryl;
the phenyl and heteroaryl groups of $R^4$ are optionally substituted with 1-2 groups independently selected from: $C_{1-4}$ alkyl, $C_{3-6}$ cycloalkyl, —$C_{1-3}$ alkylene-$C_{3-6}$ cycloalkyl, F, Cl, Br, I, —CN, $OR^a$, $SR^a$, $NR^aR^b$, $CF_3$, $OCF_3$, $COR^a$, $CO_2R^a$, $C(O)NR^aR^b$, $OC(O)R^a$, $OCO_2R^a$, $OC(O)NR^aR^b$, $NR^bCOR^a$, $NR^bCO_2R^a$, $NR^b$-$C(O)NR^aR^b$, and $S(O)_pNR^aR^b$;
each $R^a$ is independently selected from: H, $C_{1-4}$ alkyl, $C_{3-6}$ cycloalkyl, and —$C_{1-3}$ alkylene-$C_{3-6}$ cycloalkyl;
each $R^b$ is independently selected from: H, $C_{1-4}$ alkyl, $C_{3-6}$ cycloalkyl, and —$C_{1-3}$ alkylene-$C_{3-6}$ cycloalkyl; and,
p is independently selected from: 0, 1, and 2.

12. A compound of claim 11, wherein:
ring $R^4$ is selected from phenyl, pyridyl, thienyl, furanyl, pyrrolyl, oxazolyl, isoxazolyl, thiazolyl, isothiazolyl, pyrimidyl, and pyridazinyl.

13. A compound of claim 12, wherein:
ring $R^4$ is selected from phenyl and pyridyl.

14. A compound of claim 13, wherein:
$R^1$ is selected from: methyl, ethyl, and cyclopropyl;
$R^2$ is selected from: methyl, ethyl, and cyclopropyl;
$R^3$ is selected from: methyl, ethyl, and -methylene-cyclopropyl;
$R^4$ is phenyl optionally substituted with 1-2 groups independently selected from: $C_{1-4}$ alkyl, $C_{3-6}$ cycloalkyl, —$C_{1-3}$ alkylene-$C_{3-6}$ cycloalkyl, F, Cl, —CN, $OR^a$, $NR^aR^b$, $CF_3$, and $OCF_3$;

each R$^a$ is independently selected from: H, methyl, and ethyl; and,
each R$^b$ is independently selected from: H, methyl, and ethyl.
15. A compound of claim 1, wherein the compound is selected from compounds 7-8:
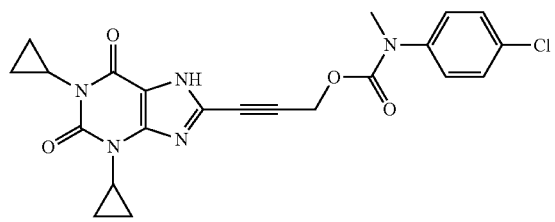
7
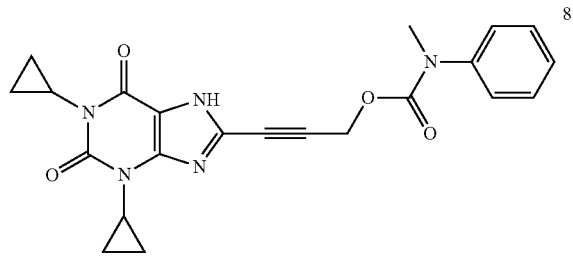
8
or a pharmaceutically acceptable salt thereof.
16. A compound of claim 1, wherein the compound is selected from compounds 35-46:
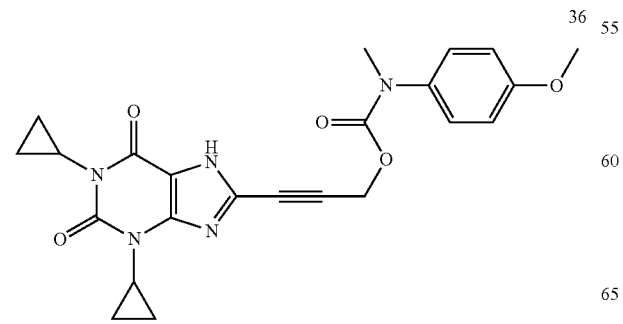
35
36
-continued
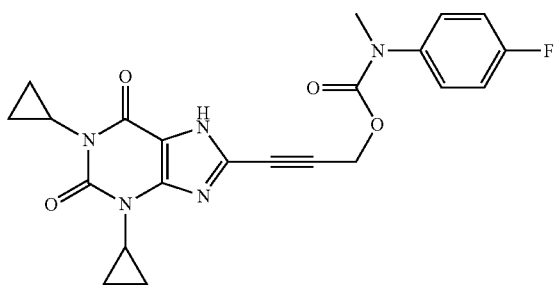
37
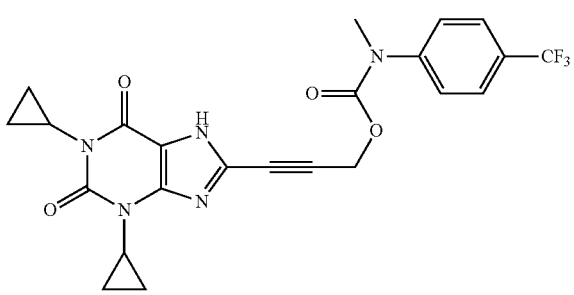
38
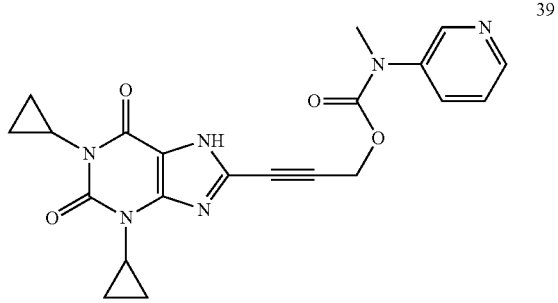
39
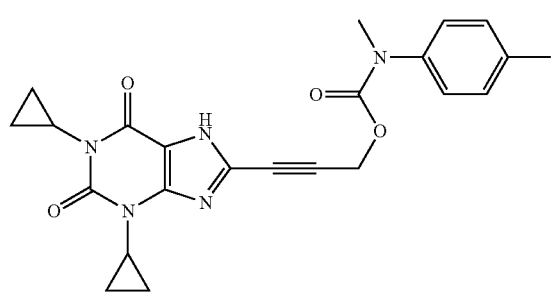 [SMILES: Cc1ccc(N(C)C(=O)OCC#Cc2nc3c([nH]2)c(=O)n(C2CC2)c(=O)n3C2CC2)cc1]
40
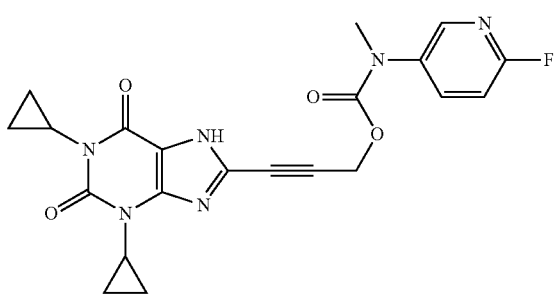 [SMILES: CN(C(=O)OCC#Cc1nc2c([nH]1)c(=O)n(C1CC1)c(=O)n2C1CC1)c1ccc(F)nc1]
41

-continued

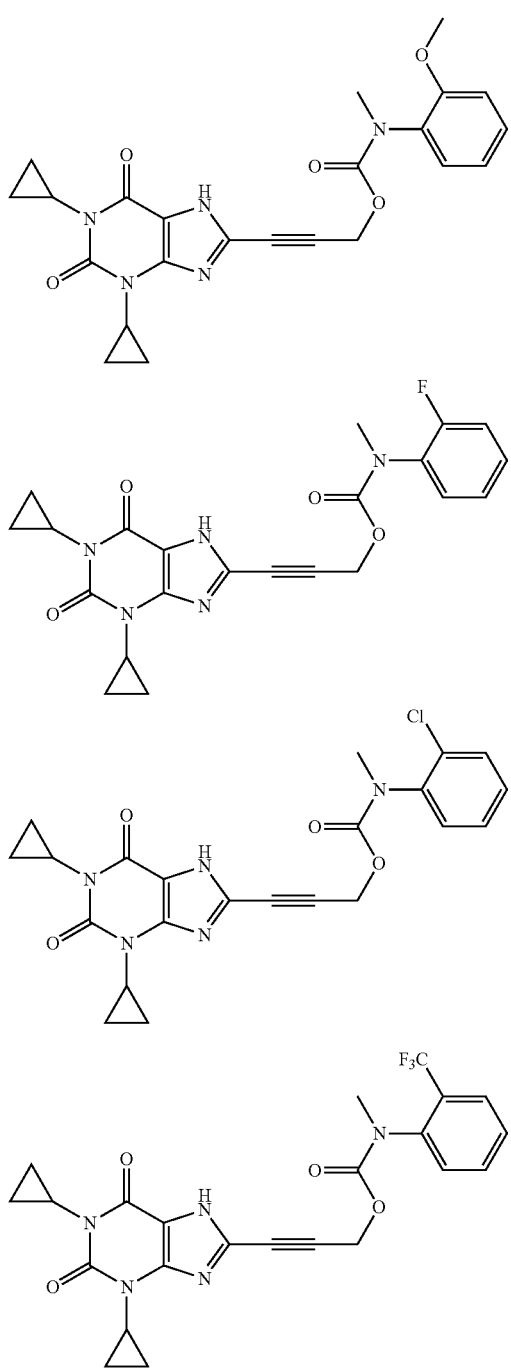

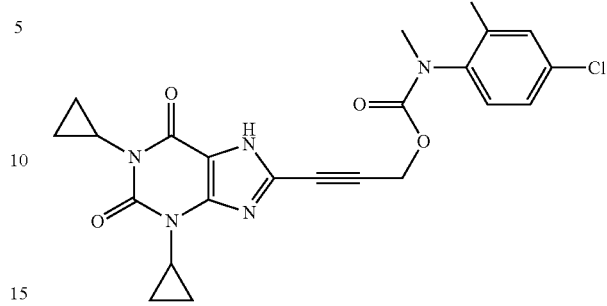

or a pharmaceutically acceptable salt thereof.

17. A pharmaceutical composition, comprising: a compound of claim 1 or a stereoisomer or pharmaceutically acceptable salt thereof and a pharmaceutically acceptable carrier.

18. A method for treating an adenosine $A_{2B}$ receptor associated state in a subject, comprising: administering to the subject an effective amount of a compound of claim 1 or a stereoisomer or pharmaceutically acceptable salt thereof.

19. The method of claim 18, wherein the adenosine $A_{2B}$ receptor associated state is selected from asthma, bronchoconstriction, chronic obstructive pulmonary disorder, angiogenesis, pulmonary fibrosis, emphysema, allergies, allergic diseases, autoimmune diseases, inflammation, atherosclerosis, hypertension, congestive heart failure, retinopathy, diarrheal diseases, insulin resistance, Type 1 diabetes, Type 2 diabetes, obesity, fatty liver disease, pain, wound healing, inflammatory gastrointestinal tract disorders, sickle cell disease, cancer, heart attack, diabetic retinopathy, hyperbaric oxygen-induced retinopathy, inhibition of angiogenesis in neoplastic tissues, gastrointestinal disorders, immunological disorders, hypersensitivity disorders, neurological disorders, and cardiovascular diseases due to both cellular hyperproliferation and apoptosis.

20. The method of claim 18, wherein the adenosine $A_{2B}$ receptor associated state is selected from: asthma, insulin resistance, atherosclerosis, fatty liver disease, bladder cancer, and breast cancer.

21. The method of claim 20, wherein the adenosine $A_{2B}$ receptor associated state is human cell line MDA-MB-231 breast cancer.

* * * * *